United States Patent [19]
O'Brien et al.

[11] Patent Number: 5,972,616
[45] Date of Patent: Oct. 26, 1999

[54] TADG-15: AN EXTRACELLULAR SERINE PROTEASE OVEREXPRESSED IN BREAST AND OVARIAN CARCINOMAS

[75] Inventors: Timothy J. O'Brien; Hirotoshi Tanimoto, both of Little Rock, Ark.

[73] Assignee: The Board of Trustees of the University of Arkansas, Little Rock, Ark.

[21] Appl. No.: 09/027,337

[22] Filed: Feb. 20, 1998

[51] Int. Cl.$^6$ .................................................. C12Q 1/68
[52] U.S. Cl. ..................... 435/6; 435/320.1; 435/69.1; 536/23.1; 536/23.5; 530/350
[58] Field of Search .................. 536/23.1, 23.5; 530/350; 435/320.1, 6, 71.2, 69.1, 41, 71.1

*Primary Examiner*—Sheela Huff
*Attorney, Agent, or Firm*—Benjamin Aaron Adler

[57] ABSTRACT

The present invention provides a DNA encoding a TADG-15 protein selected from the group consisting of: (a) isolated DNA which encodes a TADG-15 protein; (b) isolated DNA which hybridizes to isolated DNA of (a) above and which encodes a TADG-15 protein; and (c) isolated DNA differing from the isolated DNAs of (a) and (b) above in codon sequence due to the degeneracy of the genetic code, and which encodes a TADG-15 protein. Also provided is a vector capable of expressing the DNA of the present invention adapted for expression in a recombinant cell and regulatory elements necessary for expression of the DNA in the cell.

11 Claims, 17 Drawing Sheets

```
RIVGGRDTSL GRWPWQVSL. ....RYDG.A HLCGGSLLSG DWVLTAAHCF PE....RNRV LSRWRVFAGA VAQASPHGLQ
RVVGGTDADE GEWPWQVSL. ....HALGQG HICGASLISP NWLVSAAHCY IDDRGFRYSD PTQWTAFLGL HDQSQRSAPG
KIIDGAPCAR GSHPWQVAL. ....LSGNQL H.CGGVLVNE RWVLTAAHC. .........K MNEYTVHLGS DTLG...DR.R
KIVGGYNCEE NSVPYQVSL. ....NSGYHF ..CGGSLINE QWVVSAGHC. .........Y KSRIQVRLGE HNIEVLEG.N
RIVNGEDAVP GSWPWQVSL. ....QDKTGF HFCGGSLISE DWVTAAHC.. .........GV RTSDVVVAGE FDQGSDEE.N
RIVGGKVCPK GECPWQVLL. ....LVNG.A QLCGGTLINT IWVVSAAHCF DKIKNWRNLI .....AVLGE HDLSEHDGDE
RIKGGLFADI ASHPWQAAIF AKHRRSPGER FLCGGILISS CWILSAAHCF QERFPPHHL. ....TVILGR .TYRVVPGEE

LGVQAVVYHG GYLPFRDPNS EENSNDIALV HLSS.PLPLT EYIQPVCLPA ...AGQALVD GKICTVTGWG NTQYYGQQ.A
VQERRLKRII SHPFFNDFTE D...YDIALL ELEK.PAEYS SMVRPICLPD ...ASHVFPA GKAIWVTGWG HTQYGGTG.A
AQRIKASKSF RHPGYSTQT. ..HVNDLMLV KLNS.QARLS SMVKKVRLPS ...RCE..PP GTTCTVSGWG TTTSPDVTFP
EQFINAAKII RHPQYDRKT. ..LNNDIMLI KLSS.RAVIN ARVSTISLPT ...APP..AT GTKCLISGWG NTASSGADYP
IQVLKIAKVF KNPKFSILT. ..VNNDITLL KLAT.PARFS QTVSAVCLPS ...ADDDFPA GTLCATTGWG KTKYNANKTP
QSRRVAQVII P....STYVP GTTNHDIALL RLHQ.PVVLT DHVVPLCLPE RTFSERTLAF VRFSLVSGWG QLLDRGATAL
EQKFEVEKYI VHKEFDDDTY D...NDIALL QLKSDSSRCA QESSVVRTVC LPPADLQLPD WTECELSGYG KHEALSPFYS
                                                                  *

GVLQEARVPI ISNDVCNGAD FYGN..QIKP KMFCAGYPEG G......IDA CQGDSGGPFV CEDSISRTPR WRLCGIVSWG  (SEQ. ID NO: 3)  Heps
LILQKGEIRV INQTTCE..N LLPQ..QITP RMMCVGFLSG G......VDS CQGDSGGPL. ..SSVEADGR IFQAGVVSWG  (SEQ. ID NO: 14) Tadg 15
SDLMCVDVKL ISPQDCTKV. .YKD..LLEN SMLCAGIPDS K......KNA CNGDSGGPLV C......R.. .GTLQGLVSWG (SEQ. ID NO: 4)  Scce
DELQCLDAPV LSQAKCEAS. .YPG..KITS NMFCVGFLEG G......KDS CQGDSGGPVV C......N.. .GQLQGVVSWG (SEQ. ID NO: 5)  Try
DKLQQAALPL LSNAECKKS. .WGR..RITD VMICAG..AS G......VSS CMGDSGGPLV C......QKDGA WTLVGIVSWG (SEQ. ID NO: 6)  Chymb
ELMVLNVPRL MTQDCLQQSR KVGDSPNITE YMFCAGYSDG S......KDS CKGDSGGP.. ..HATHYRGT WYLTGIVSWG (SEQ. ID NO: 7)  Fac 7
ERLKEAHVRL YPSSRCTSQH LLNRT..VTD NMLCAGDTRS GGPQANLHDA CQGDSGGPLV CLN....DGR MTLVGIISWG (SEQ. ID NO: 8)  Tpa T.GCALAQKP GVYTKVSDFR EWIFQAIKTH SEASGMVTQL ~~         (SEQ. ID NO: 3)   Heps
D.GCAQRNKP GVYTRLPLFR DWIKENTGV~ ~~~~~~~~~~ ~~         (SEQ. ID NO: 14)  Tadg 15
TFPCGQPNDP GVYTQVCKFT KWINDTMKKH R~~~~~~~~~ ~~         (SEQ. ID NO: 4)   Scce
D.GCAQKNKP GVYTKVYNYV KWIKNTIAAN S~~~~~~~~~ ~~         (SEQ. ID NO: 5)   Try
SDTCS.TSSP GVYARVTKLI PWVQKILAAN ~~~~~~~~~~ ~~         (SEQ. ID NO: 6)   Chymb
Q.GCATVGHF GVYTRVSQYI EWLQKLMRSE PRPGVLLRAP FP         (SEQ. ID NO: 7)   Fac 7
.LGCGQKDVP GVYTKVTNYL DWIRDNMRP~ ~~~~~~~~~~ ~~         (SEQ. ID NO: 8)   Tpa
```

```
  1 TCAAGAGCGGGCCTCGGGGTACCATGGGGAGCGATCGGGCCAAGGGGCCCGAAGGACTTCGGCGGGACTC
                       M  G  S  D  R  A  R  K  G  G  G  P  K  D  F  G  A  G  L

83 AAGTACAACTCCCGGCACGAGAAAGTGAATGGCTTGGAGGAAGGCGTTCCTGCCAGTCAACAACGTCAAGAAGGTG
     K  Y  N  S  R  H  E  K  V  N  G  L  E  E  G  V  E  F  L  P  V  N  N  V  K  K  V

164 GAAAAGCATGGCCCGGGCCGCTGGGTGGTGCTGGCTGCTGCCGTGCTGATCGGCCTCCTCTTGGTCTTGCTGGGGATCGGCTTC
     E  K  H  G  P  G  R  W  V  V  L  A  A  V  L  I  G  L  L  L  V  L  L  G  I  G  F

245 CTGGTGTGGCATTTGCAGTACCGGGACGTGCGTGTCCAGAAGGTCTTCAATGGCTACATGAGGATCACAAATGAGAATTTT
     L  V  W  H  L  Q  Y  R  D  V  R  V  Q  K  V  F  N  G  Y  M  R  I  T  N  E  N  F

326 GTGGATGCCTACGAGAACTCCAACTCCGAGTTTGTAAGCCTGGCCAGCAAGGTGAAGGACGCGCTGAAGCTGCTGTAC
     V  D  A  Y  E  N  S  N  S  T  E  F  V  S  L  A  S  K  V  K  D  A  L  K  L  L  Y

407 AGCGGAGTCCCATTCCTGGGCCCCTACCACAAGGAGTCGGCTGTGACGGCCTTCAGCGAGGGCTCAGCGTCATCGCCTACTAC
     S  G  V  P  F  L  G  P  Y  H  K  E  S  A  V  T  A  F  S  E  G  S  V  I  A  Y  Y

488 TGGTCTGAGTTCAGCATCCCGCAGCACCTGGTGGAGGAGGCCGAGCGCGTCATGGCCGAGGAGCGCGTAGTCATGCTGCCC
     W  S  E  F  S  I  P  Q  H  L  V  E  E  A  E  R  V  M  A  E  E  R  V  M  L  P

569 CCGCGGGCGCGCTCCCTGAAGTCCTTTGTGTGTCAGTGGTGGCTTCACCTCAGTCCCAAAACAGTACAGAGGACC
     P  R  A  R  S  L  K  S  F  V  V  T  S  V  V  A  F  P  T  D  S  K  T  V  Q  R  T

650 CAGGACAACAGCTGCCATGCCCGGCTGCACGCGCCGGTGTGGAGCTGATGCGCTTCACCACGCCCGGCTTCCCTGACAGC
     Q  D  N  S  C  S  F  G  L  H  A  R  G  V  E  L  M  R  F  T  T  P  G  F  P  D  S

731 CCCTACCCCGCTCATGCCCGCTGCCAGTGGGCCCTGCGGGGACGCGACTCAGTGCTGAGCCTCACCTTCCGCAGCTTT
     P  Y  P  A  H  A  R  C  Q  W  A  L  R  G  D  A  D  S  V  L  S  L  T  F  R  S  F

812 GACCTTGCGTCCTGCGACGAGCGCGGCAGCGACCTGGTGACAGTGTACAACACCCTGAGCCCCATGGAGCCCCACGCCCTG
     D  L  A  S  C  D  E  R  G  S  D  L  V  T  V  Y  N  T  L  S  P  M  E  P  H  A  L

893 GTGCAGTTGTGTGGCACCTACCCTCCCTCCTACAACCTGACCTTCCACTCCTCCCAGAACGTCCTGCTCATCACACTGATA
     V  Q  L  C  G  T  Y  P  P  S  Y  N  L  T  F  H  S  S  Q  N  V  L  L  I  T  L  I
```

```
 974 ACCAACACTGAGCGGCGGCATCCCGGCTTTGAGGCTTCTTCCAGCTGCCTAGGATGAGCAGTCTGTGGAGGCCGCTTA
      T  N  T  E  R  R  H  P  G  F  E  A  T  F  F  Q  L  P  R  M  S  S  C  G  G  R  L
1055 CGTAAAGCCCAGGGGACATTCAACAGCCCCACTACTACCCAGGCCACCCCAACATTGACTGCACATGGAACATTGAG
      R  K  A  Q  G  T  F  N  S  P  Y  Y  P  G  H  Y  P  P  N  I  D  C  T  W  N  I  E
1136 GTGCCCAACAACCAGCATGTGAAGGTGAGCTTCAAATTCTTCTACCTGCTTGAGCCCGGCGTGCCGGGCACTGCCCC
      V  P  N  N  Q  H  V  K  V  S  F  K  F  F  Y  L  L  E  P  G  V  P  A  G  T  C  P
1217 AAGGACTACGTGGAGATCAATGGGGAGAAATACTGCGGAGAGAGGTCCCAGTTCGTCGTCACCAGCAACAGCAAGATC
      K  D  Y  V  E  I  N  G  E  K  Y  C  G  E  R  S  Q  F  V  V  T  S  N  S  N  K  I
1298 ACAGTTCGCTTCCACTCAGATCAGTCCTACACAGACACCGGCTTCTTAGCTGAATACCTCTCCAGTGACTGACCCA
      T  V  R  F  H  S  D  Q  S  Y  T  D  T  G  F  L  A  E  Y  L  S  Y  D  S  S  D  P
1379 TGCCCGGGGCAGTTCACGTGCCGCACTGGCTGTATCCGGAAGGAGCTGCGCTGTGATGGCTGGGCCGACTGCACCGAC
      C  P  G  Q  F  T  C  R  T  G  R  C  I  R  K  E  L  R  C  D  G  W  A  D  C  T  D
1460 CACAGCGATGAGCTCAACTGTGAAGACTGCGGAGACAACAGCGACGAGCAGGGTGCAAGTTCTGCAAGCCCCTTCTGG
      H  S  D  E  L  N  C  S  C  D  A  G  H  Q  F  T  C  K  N  K  F  C  K  P  L  F  W
1541 GTCTGCGACAGTGCCTCTGAACGACTGCAGTTCACGTGCCGCCCCAGACTTGTCCGGCCCCAGACCTTCAGGTGTTCC
      V  C  D  S  V  N  D  C  G  D  N  S  D  E  Q  G  C  S  C  P  A  Q  T  F  R  C  S
1622 AATGGGAAGTGCCTCTGCAAAGCCAGTCAGCAGTGCAATGGAAGGACTGTGGGACGACTGCGGGGACGAGGCCTCCCC
      N  G  K  C  L  S  K  S  Q  Q  C  N  G  K  D  D  C  G  D  G  S  D  E  A  S  C  P
1703 AAGGTGAACGTGACTTGTCACTTGTACCAAACACACTGCCTCAATGGCCTCTGCTTGAGCAAGGCAACCCTGAGTGT
      K  V  N  V  T  C  H  T  Y  R  C  L  N  G  L  C  L  S  K  G  N  P  E  C
1784 GACGGGAAGGAGGACTGTAGCGACGGCTCAGATGAGGGCAGTGCTGCCCTGCGACTGTGGCGTCATTCACGAGACAGGCTCGT
      D  G  K  E  D  C  S  D  G  S  D  E  K  D  C  D  C  G  L  R  S  F  T  R  Q  A  R
1865 GTTGTTGGGGGCACGGATGCGGATGAGGGCGAGTGGCCCTGGCAGGTAAGCCTCCATGCTCTGGGCCAGGGCCACATCTGC
      V  V  G  G  T  D  A  D  E  G  E  W  P  W  Q  V  S  L  H  A  L  G  Q  G  H  I  C
1946 GGTGCTTCCCTCATCTCTCCCAACTGGCTGGTCTCTGCCGCACACTGCTACATCGATGACGACAGAGGATTCAGTGACTCAGAC
      G  A  S  L  I  S  P  N  W  L  V  S  A  A  [C] Y  I  D  D  R  G  F  R  Y  S  D
```

FIG. 9-2

```
2027  CCCACGCAGTGGACGGCCTTCCTGGGCTTGCACGAGGACCAGAGCCAGCGCCCCTGGGTGCAGGAGGCGCAGGCTCAAG
      P  T  Q  W  T  A  F  L  G  L  H  D  Q  S  Q  R  S  A  P  G  V  Q  E  R  R  L  K

2108  CGCATCATCTCCCACCCCTTCTTCAATGACTTCACCTTCGACTATGACATCGCGCTGCTGGAGCTGGAGAAACCGGCAGAG
      R  I  I  S  H  P  F  F  N  D  F  T  F  D  Y  [D] I  A  L  L  E  L  E  K  P  A  E

2189  TACAGCTCCATGGTGCGGCCCATCTGCCTGCCCGACGCCTCCCATGTCTTCCCGGCAAGGCCATCTGGGTCACGGGC
      Y  S  S  M  V  R  P  I  C  L  P  D  A  S  H  V  F  P  A  G  K  A  I  W  V  T  G

2270  TGGGGACACACCAGTATGGAGGCACTGGCGCTGATCCTGCAAAAGGGTGAGATCCGCGTCATCAACCAGACCACCTGC
      W  G  H  T  Q  Y  G  G  T  G  A  L  I  L  Q  K  G  E  I  R  V  I  N  Q  T  T  C

2351  GAGAACCTCCTGCCGCAGCAGATCACGCCCCGCATGATGTGCGTGGGCTTCCTCAGCGGCGTGGACTCCTGCCAGGGT
      E  N  L  L  P  Q  Q  I  T  P  R  M  M  C  V  G  F  L  S  G  V  D  S  C  Q  G

2432  GATTCCGGGGGACCCCTGTCCAGCGTGGAGGCGGATCTTCCAGGCGGGATCTTCCAGGCTTCCAGGCTTCCCTGTTGCGGGACTGAGATCAAAGAGAACACTGGGTATAGGGG
      D  [G] G  P  L  S  S  V  E  A  D  G  R  I  F  Q  A  G  V  V  S  W  G  D  G  C

2513  GCTCAGAGGAACAAGCCAGGCGTGTACACACAAGGCTCCCCTGTTTCGGGACTGATCAAAGAGAACACTGGGTATAGGG
      A  Q  R  N  K  P  G  V  Y  T  R  L  P  L  F  R  D  W  I  K  E  N  T  G  V (SEQ. ID NO: 2)

2594  CCGGGGGCCACCCAGAATGTGTACACCCTGCGGGCCACCATCGTCCACCCCAGTGTGCACGCCTGCAGGCTGGAGACTGGAC
2675  CGCTGACTGCACCCAGCCTCCAAAGTGCGCCCCCAGAACATACACTGTGAACTCCAATCTGCAGGCTCCAAATCTGCTAGAAAACCTCTCGC
2756  TTCCTCAGCCTCCAAAGTCCCCCGCCAGCCTCCAAAGCTGGAGGTAGAAGGGACCACTGGTGTTGTTCTACTGACCAACTGGGGCAAAGTT
2837  TGAAGACACAGCCTGGGAGCTTCGGACCTCCCCAGCTGGGCCAAGCTGGGCCGAGGGCGTTTGTGTATCGCCCCTGTCTGTAAGGAGC
2918  AGCGGGAACGGACCGCCAGGCTGCCCTCAGTGAAGTGGCCGATCTGGGCGTGGGCCTTGGGCCACGCT
2999  CTTGAGGAAGCCCAGGCTGGCTGGAGGACACGGGTCTGAGAAACAGACAATTATTTCTTTTTAAAAATGTTTTACCAGCTCCCAGGGTGGA
3080  CTTCAGTGTGTGTATTGTGTAAATGGGGTAAAACAATTATTTCTTTTTAAAAAAAAAAAAAAAAA (SEQ. ID NO: 1)

──── : KOZAK'S CONSENSUS SEQUENCE
==== : TRANSMEMBRANE DOMAIN
 □   : CONSERVED AMINO ACIDS OF CATALYTIC TRIAD H, D, S

FIG. 9-3
```

```
  1  MGSDRARKGG GGPKDFGAGL KYNSRHEKVN GLEEGVEFLP VNNVKKVEKH    1
 51  GPGRWVVLAA VLIGLLLVLL GIGFLVWHLQ YRDVRVQKVF NGYMRITNEN    2
101  FVDAYENSNS TEFVSLASKV KDALKLLYSG VPFLGPYHKE SAVTAFSEGS
151  VIAYYWSEFS IPQHLVEEAE RVMAEERVVM LPPRARSLKS FVVTSVVAFP
201  TDSKTVQRTQ DNSCSFGLHA RGVELMRFTT PGFPDSPYPA HARCQWALRG
251  DADSVLSLTF RSFDLASCDE RGSDLVTVYN TLSPMEPHAL VQLCGTYPPS
301  YNLTFHSSQN VLLITLITNT ERRHPGFEAT FFQLPRMSSC GGRLRKAQGT    3
351  FNSPYYPGHY PPNIDCTWNI EVPNNQHVKV SFKFFYLLEP GVPAGTCPKD
401  YVEINGEKYC GERSQFVVTS NSNKITVRFH SDQSYTDTGF LAEYLSYDSS
451  DPCPGQFTCR TGRCIRKELR CDGWADCTDH SDELNCSCDA GHQFTCKNKF
501  CKPLFWVCDS VNDCGDNSDE QGCSCPAQTF RCSNGKCLSK SQQCNGKDDC
551  GDCSDEASCP KVNVVTCTKH TYRCLNGLCL SKGNPECDGK EDCSDCSDEK    4
601  DCDCGLRSFT RQARVVGGTD ADEGEWPWQV SLHALGQGHI CGASLISPNW
651  LVSAAHCYID DRGFRYSDPT QWTAFLGLHD QSQRSAPGVQ ERRLKRIISH
701  PFFNDFTFDY DIALLELEKP AEYSSMVRPI CLPDASHVFP AGKAIWVTGW    5
751  GHTQYGGTGA LILQKGEIRV INQTTCENLL PQQITPRMMC VGFLSGGVDS
801  CQGDSGGPLS SVEADGRIFQ AGVVSWGDGC AQRNKPGVYT RLPLFRDWIK
851  ENTGV   (SEQ. ID NO: 2)
```

* : Conserved cysteine residue
NXT : Possible N-linked glycosylation site
SDE : Conserved SDE motif
▼ : Potential cleavage site
Ⓞ : Conserved amino acids of catalytic triad H, D, S 1. Cytoplasmic domain
2. Transmembrane domain
3. CUB repeat
4. Ligand-binding repeat (class A motif) of LDL receptor like domain
5. Serine protease

FIG. 10

1. Cytoplasmic domain
2. Transmembrane domain
3. Extracellular domain
4-5. CUB repeat
6-9. Ligand-binding repeat (class A motif) of LDL receptor like domain
10. Serine protease

```
1575  GCGACGAGCAGGGTGCAGTTGTCCGG.CCCAGACCTTCAGGTGTTCCAATGGAAGTGCCTCTCGAAAAGCCAGCAGTGCAATGGAAGGACGACTGTG  1673
      ||||||||||||||||  ||| ||||  |||||||||||||||||||||||||||||||||||||||||||||||||||||||||||||||||||
1378  GCGACGAGCAGGGTTGCATTTGTCCGGACCCAGACCTTCAGGTGTTCCAATGGAAGTGCCTCTCGAAAAGCCAGCAGTGCAATGGAAGGACGACTGTG  1477

1674  GGGACGGGTCCGACGAGAGGCCTCCTGCCCCAAGGTGAACGTCGTCACTGTACCAAACACACTACGCTGCCTCAATGGGCTCTGCTTGAGCAAGGCAA  1773
      ||||||||||||||||||||||||||||||||||||||||||||||||||||||||||||||||||||||||||||||||||||||||||||||||
1478  GGGACGGGTCCGACGAGAGGCCTCCTGCCCCAAGGTGAACGTCGTCACTGTACCAAACACACTACGCTGCCTCAATGGGCTCTGCTTGAGCAAGGCAA  1577

1774  CCCTGAGTGTGACGGGAAGGAGACTGTAGCGACGCTCAGATGAGAAGGACTGCGACTGCGCGTGCGACTGTGGGCTGCGCGTCATTCACGAGACAGGCTCGTGTTGTTGGG  1873
      ||||||||||||||||||||||||||||||||||||||||||||||||||||||||||||||||||||||||||||||||||||||||||||||||
1578  CCCTGAGTGTGACGGGAAGGAGACTGTAGCGACGCTCAGATGAGAAGGACTGCGACTGCGCGTGCGACTGTGGGCTGCGCGTCATTCACGAGACAGGCTCGTGTTGTTGGG  1677

1874  GGCACGGATGCGGATGAGGGCGAGTGCTCTGGGCCAGGCCTAAGCCTGCATGCCGGTGCTTCCCTCATCTCTCCCAACTGGC  1973
      ||||||||||||||||||||||||||||||||||||||||||||||||||||||||||||||||||||||||||||||||
1678  GGCACGGATGCGGATGAGGGCGAGTGCTCTGGGCCAGGCCTAAGCCTGCATGCCGGTGCTTCCCTCATCTCTCCCAACTGGC  1777

1974  TGGTCTCTGCCGCCACACTGCTACATCGATGACAGAGGATTCAGTACTCAGACCCCACGCAGTGACGGCCTTCCTGGGCTTGCACGACCAGCCAGCG  2073
      |||||||||||||||||||||||||||||||||||||||||||||||||||||       |||||||||||||||||||||||||||||||||||
1778  TGGTCTCTGCCGCCACACTGCTACATCGATGACAGAGGATTCAGTACTCAGACCCCACGCA..GACGCGGCCTTCCTGGGCTTGCACGACCAGCCAGCG  1875

2074  CAGCGCCCCTGGGGTGCAGGAGCAGCGCCAGGCTCAAGCGCATCATCTCCCACCCCTTCTTCAATGACTTCACCTTCGACTATGACATCGCGCTGCTGGAGCTG  2173
      ||  |  ||||||||||||||||||||||||||||||||||||||||||||||||||||||||||||||||||||||||||||||||||||||||
1876  CA..GGCCCTGGGGTGCAGGAGCAGCGCCAGGCTCAAGCGCATCATCTCCCACCCCTTCTTCAATGACTTCACCTTCGACTATGACATCGCGCTGCTGGAGCTG  1973

2174  GAGAAACCGGCAGAGTACAGCTCCATGGTGCGGCCCATGTCTTCCCTGCCGCGGCCAAGGCCATCTGGGTCACGGGCTGGG  2273
      ||||||||||||||||||||||||||||||||||||||||||||||||||||||||||||||||||||||||||||||||
1974  GAGAAACCGGCAGAGTACAGCTCCATGGTGCGGCCCATGTCTTCCCTGCCGCGGCCAAGGCCATCTGGGTCACGGGCTGGG  2073

2274  GACACACCCAGTATGGAGGCACTGGCGCGCTGATCCTGCAAAAGGGTGAGATCCGCGTCATCAACCAGACCACCTGCCGAGAACCTCGCCGCAGCAGAT  2373
      ||||||||||||||||||||||||||||||||||||||||||||||||||||||||||||||||||||||||||||||||||||||||||||||||
2074  GACACACCCAGTATGGAGGCACTGGCGCGCTGATCCTGCAAAAGGGTGAGATCCGCGTCATCAACCAGACCACCTGCCGAGAACCTCGCCGCAGCAGAT  2173
```

TADG-15: AN EXTRACELLULAR SERINE PROTEASE OVEREXPRESSED IN BREAST AND OVARIAN CARCINOMAS

BACKGROUND OF THE INVENTION

1. Field of the Invention

The present invention relates generally to the fields of cellular biology and the diagnosis of neoplastic disease. More specifically, the present invention relates to an extracellular serine protease termed Tumor Antigen Derived Gene-15 (TADG-15), which is overexpressed in breast and ovarian carcinomas.

2. Description of the Related Art

Extracellular proteases have been directly associated with tumor growth, shedding of tumor cells and invasion of target organs. Individual classes of proteases are involved in, but not limited to (1) the digestion of stroma surrounding the initial tumor area, (2) the digestion of the cellular adhesion molecules to allow dissociation of tumor cells; and (3) the invasion of the basement membrane for metastatic growth and the activation of both tumor growth factors and angiogenic factors.

The prior art is deficient in the lack of effective means of screening to identify proteases overexpressed in carcinoma. The present invention fulfills this longstanding need and desire in the art.

SUMMARY OF THE INVENTION

The present invention discloses a screening program to identify proteases overexpressed in carcinoma by examining PCR products amplified using differential display in early stage tumors, metastatic tumors compared to that of normal tissues.

In one embodiment of the present invention, there is provided a DNA encoding a TADG-15 protein selected from the group consisting of: (a) isolated DNA which encodes a TADG-15 protein; (b) isolated DNA which hybridizes to isolated DNA of (a) above and which encodes a TADG-15 protein; and (c) isolated DNA differing from the isolated DNAs of (a) and (b) above in codon sequence due to the degeneracy of the genetic code, and which encodes a TADG-15 protein.

In another embodiment of the present invention, there is provided a vector capable of expressing the DNA of the present invention adapted for expression in a recombinant cell and regulatory elements necessary for expression of the DNA in the cell.

In yet another embodiment of the present invention, there is provided a host cell transfected with the vector of the present invention, the vector expressing a TADG-15 protein.

In still yet another embodiment of the present invention, there is provided a method of detecting expression of a TADG-15 mRNA, comprising the steps of: (a) contacting mRNA obtained from the cell with the labeled hybridization probe; and (b) detecting hybridization of the probe with the mRNA.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows a comparison of the serine protease catalytic domain of TADG-15 with hepsin (Heps, SEQ ID No: 3), (Scce, SEQ ID No: 4), trypsin (Try, SEQ ID No: 5), chymotrypsin (Chymb, SEQ ID No: 6), factor 7 (Fac7, SEQ ID No: 7) and tissue plasminogen activator (Tpa, SEQ ID No: 8). The asterisks indicate conserved amino acids of catalytic triad.

FIG. 9 shows nucleotide sequence of the TADG-15 cDNA (SEQ ID No: 1) and amino acid sequence of the TADG-15 protein (SEQ ID No: 2)

FIG. 10 shows the amino acid sequence of the TADG-15 protease including functional sites and domains.

FIG. 12 shows a nucleotide sequence comparison between TADG-15 and human SNC-19 (GeneBank accession #U20428).

DETAILED DESCRIPTION OF THE INVENTION

Figure 1:
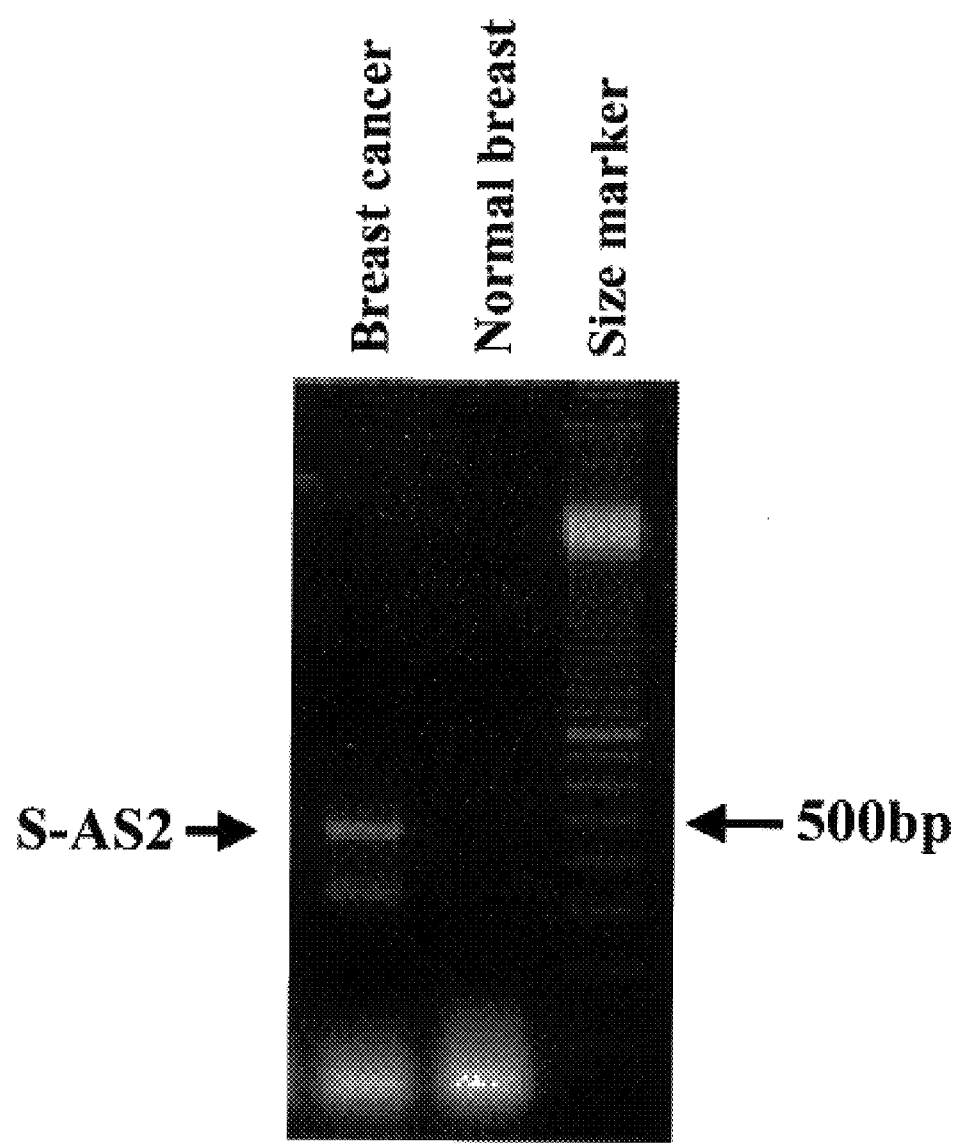
FIG. 1 shows a comparison of PCR products derived from normal and breast carcinoma cDNA as shown by staining in an agarose gel.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The TADG-15 cDNA is 3147 base pairs long (SEQ ID No:1) and encoding for a 855 amino acid protein (SEQ ID No:2). The availability of the TADG-15 gene opens the way for a number studies that can lead to various applications. For example, the TADG-15 gene can be used as a diagnostic or therapeutic target in ovarian carcinoma and other carcinomas including breast, prostate, lung and colon.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the -10 and -35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human TADG-15 protein of the present invention can be used to transform a host using any of the techniques commonly known to those of ordinary skill in the art. Especially preferred is the use of a vector containing coding sequences for the gene which encodes a human TADG-15 protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a TADG-15 protein, a strand of which DNA will hybridize at high stringency to a probe containing a sequence of at least 15 consecutive nucleotides of (SEQ ID NO: 1). The protein encoded by the DNA of this invention may share at least 80% sequence identity (preferably 85%, more preferably 90%, and most preferably 95%) with the amino acids listed in FIG. 10 (SEQ ID NO:2). More preferably, the DNA includes the coding sequence of the nucleotides of FIG. 9 (SEQ ID NO: 1), or a degenerate variant of such a sequence.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in FIG. 9 (SEQ ID NO:1) or the complement thereof. Such a probe is useful for detecting expression of TADG-15 in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from nucleotides 1 to 3147 of the nucleotides listed in FIG. 9 (SEQ ID NO:1).

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in FIG. 9 (SEQ ID NO: 1) which encodes an alternative splice variant of TADG-15.

The DNA may have at least about 70% sequence identity to the coding sequence of the nucleotides listed in FIG. 9 (SEQ ID NO:1), preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence which encodes a human TADG-15 protein and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No:1. A "vector" may be defined as a replicable nucleic acid construct, e.g., a plasmid or viral nucleic acid. Vectors may be used to amplify and/or express nucleic acid encoding TADG-15 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen.

Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure TADG-15 protein may be obtained, for example, by extraction from a natural source; by expression of a recombinant nucleic acid encoding an TADG-15 polypeptide; or by chemically synthesizing the protein. Purity can be measured by any appropriate method, e.g., column chromatography such as immunoaffinity chromatography using an antibody specific for TADG-15, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the TADG-15 protein (SEQ ID No:2). As used herein, "fragment," as applied to a polypeptide, will ordinarily be at least 10 residues, more typically at least 20 residues, and preferably at least 30 (e.g., 50) residues in length, but less than the entire, intact sequence. Fragments of the TADG-15 protein can be generated by methods known to those skilled in the art, e.g., by enzymatic digestion of naturally occurring or recombinant TADG-15 protein, by recombinant DNA techniques using an expression vector that encodes a defined fragment of TADG-15, or by chemical synthesis. The ability of a candidate fragment to exhibit a characteristic of TADG-15 (e.g., binding to an antibody specific for TADG-15) can be assessed by methods described herein. Purified TADG-15 or antigenic fragments of TADG-15 can be used to generate new antibodies or to test existing antibodies (e.g., as positive controls in a diagnostic assay) by employing standard protocols known to those skilled in the art. Included in this invention are polyclonal antisera generated by using TADG-15 or a fragment of TADG-15 as the immunogen in, e.g., rabbits. Standard protocols for monoclonal and polyclonal antibody production known to those skilled in this art are employed. The monoclonal antibodies generated by this procedure can be screened for the ability to identify recombinant TADG-15 cDNA clones, and to distinguish them from known cDNA clones.

Further included in this invention are TADG-15 proteins which are encoded at least in part by portions of SEQ ID NO:2, e.g., products of alternative mRNA splicing or alternative protein processing events, or in which a section of TADG-15 sequence has been deleted. The fragment, or the intact TADG-15 polypeptide, may be covalently linked to another polypeptide, e.g. which acts as a label, a ligand or a means to increase antigenicity.

The invention also includes a polyclonal or monoclonal antibody which specifically binds to TADG-15. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^{3}H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) *Clin. Chim. Acta* 70, 1–31; and Schurs et al., (1977) *Clin. Chim. Acta* 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting TADG-15 protein in a biological sample, which includes the steps of contacting the sample with the labeled antibody, e.g., radioactively tagged antibody specific for TADG-15, and determining whether the antibody binds to a component of the sample.

As described herein, the invention provides a number of diagnostic advantages and uses. For example, the TADG-15 protein is useful in diagnosing cancer in different tissues since this protein is highly overexpressed in tumor cells. Antibodies (or antigen-binding fragments thereof) which bind to an epitope specific for TADG-15, are useful in a method of detecting TADG-15 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labeled antibody (e.g., radioactively tagged antibody) specific for TADG-15, and detecting the TADG-15 protein using standard immunoassay techniques such as an ELISA. Antibody binding to the biological sample indicates that the sample contains a component which specifically binds to an epitope within TADG-15.

Likewise, a standard Northern blot assay can be used to ascertain the relative amounts of TADG-15 mRNA in a cell or tissue obtained from a patient suspected of having cancer, in accordance with conventional Northern hybridization techniques known to those of ordinary skill in the art. This Northern assay uses a hybridization probe, e.g. radiolabelled TADG-15 cDNA, either containing the full-length, single stranded DNA having a sequence complementary to SEQ ID NO:1 (FIG. 9), or a fragment of that DNA sequence at least 20 (preferably at least 30, more preferably at least 50, and most preferably at least 100 consecutive nucleotides in length). The DNA hybridization probe can be labeled by any of the many different methods known to those skilled in this art.

Antibodies to the TADG-15 protein can be used in an immunoassay to detect increased levels of TADG-15 protein expression in tissues suspected of neoplastic transformation. These same uses can be achieved with Northern blot assays and analyses.

The present invention is directed to DNA encoding a TADG-15 protein selected from the group consisting of: (a) isolated DNA which encodes a TADG-15 protein; (b) isolated DNA which hybridizes to isolated DNA of (a) above and which encodes a TADG-15 protein; and (c) isolated DNA differing from the isolated DNAs of (a) and (b) above in codon sequence due to the degeneracy of the genetic code, and which encodes a TADG-15 protein. Preferably, the DNA has the sequence shown in SEQ ID No:1. More preferably, the DNA encodes a TADG-15 protein having the amino acid sequence shown in SEQ ID No:2.

The present invention is also directed to a vector capable of expressing the DNA of the present invention adapted for expression in a recombinant cell and regulatory elements necessary for expression of the DNA in the cell. Preferably, the vector contains DNA encoding a TADG-15 protein having the amino acid sequence shown in SEQ ID No:2.

The present invention is also directed to a host cell transfected with the vector described herein, said vector expressing a TADG-15 protein. Representative host cells include consisting of bacterial cells, mammalian cells and insect cells.

The present invention is also directed to a isolated and purified TADG-15 protein coded for by DNA selected from the group consisting of: (a) isolated DNA which encodes a TADG-15 protein; (b) isolated DNA which hybridizes to isolated DNA of (a) above and which encodes a TADG-15 protein; and (c) isolated DNA differing from the isolated DNAs of (a) and (b) above in codon sequence due to the degeneracy of the genetic code, and which encodes a TADG-15 protein. Preferably, the isolated and purified TADG-15 protein of claim 9 having the amino acid sequence shown in SEQ ID No:2.

The present invention is also directed to a method of detecting expression of the protein of claim 1, comprising the steps of: (a) contacting mRNA obtained from the cell with the labeled hybridization probe; and (b) detecting hybridization of the probe with the mRNA.

The following examples are given for the purpose of illustrating various embodiments of the invention and are not meant to limit the present invention in any fashion.

EXAMPLE 1
Tissue collection and storage

Upon patient hysterectomy, bilateral salpingooophorectomy, or surgical removal of neoplastic tissue, the specimen is retrieved and placed it on ice. The specimen was then taken to the resident pathologist for isolation and identification of specific tissue samples. Finally, the sample was frozen in liquid nitrogen, logged into the laboratory record and stored at −80° C. Additional specimens were frequently obtained from the Cooperative Human Tissue Network (CHTN). These samples were prepared by the CHTN and shipped to us on dry ice. Upon arrival, these specimens were logged into the laboratory record and stored at −80° C.

EXAMPLE 2
mRNA isolation and cDNA synthesis

Forty-one ovarian tumors (10 low malignant potential tumors and 31 carcinomas) and 10 normal ovaries were obtained from surgical specimens and frozen in liquid nitrogen. The human ovarian carcinoma cell lines SW 626 and Caov 3, the human breast carcinoma cell lines MDA-MB-231 and MDA-MB-435S, and the human uterine cervical carcinoma cell line Hela were purchased from the American Type Culture Collection (Rockville, Md.). Cells were cultured to subconfluency in Dulbecco's modified Eagle's medium, suspended with 10% (v/v) fetal bovine serum and antibiotics.

Messenger RNA (mRNA) isolation was performed according to the manufacturer's instructions using the Mini RiboSep™ Ultra mRNA isolation kit purchased from Becton Dickinson (cat. #30034). This was an oligo(dt) chromatography based system of mRNA isolation. The amount of mRNA recovered was quantitated by UV spectrophotometry.

First strand complementary DNA (cDNA) was synthesized using 5.0 mg of mRNA and either random hexamer or oligo(dT) primers according to the manufacturer's protocol utilizing a first strand synthesis kit obtained from Clontech (cat.# K1402-1). The purity of the cDNA was evaluated by PCR using primers specific for the p53 gene. These primers span an intron such that pure cDNA can be distinguished from cDNA that is contaminated with genomic DNA.

EXAMPLE 3
PCR reactions

The mRNA overexpression of TADG-15 was determined using a quantitative PCR. Oligonucleotide primers were used for: TADG-15, forward 5'-ATGACAGAGGATTCAGGTAC-3' and reverse 5'-GAAGGTGAAGTCATTGAAGA-3'; and β-tubulin, forward 5'-TGCATTGACAACGAGGC-3' and reverse 5'-CTGTCTTGACATTGTTG-3'. β-tubulin was utilized as an internal control. Reactions were carried out as follows: first strand cDNA generated from 50 ng of mRNA will be used as template in the presence of 1.0 mM $MgCl_2$, 0.2 mM dNTPs, 0.025 U Taq polymerase/ml of reaction, and 1×buffer supplied with enzyme. In addition, primers must be added to the PCR reaction. Degenerate primers which may amplify a variety of cDNAs are used at a final concentration of 2.0 mM each, whereas primers which amplify specific cDNAs are added to a final concentration of 0.2 mM each.

After initial denaturation at 95° C. for 3 minutes, thirty cycles of PCR are carried out in a Perkin Elmer Gene Amp 2400 thermal cycler. Each cycle consists of 30 seconds of denaturation at 95° C., 30 seconds of primer annealing at the appropriate annealing temperature, and 30 seconds of extension at 72° C. The final cycle will be extended at 72° C. for 7 minutes. To ensure that the reaction succeeded, a fraction of the mixture will be electrophoresed through a 2% agarose/TAE gel stained with ethidium bromide (final concentration 1 mg/ml). The annealing temperature varies according to the primers that are used in the PCR reaction. For the reactions involving degenerate primers, an annealing temperature of 48° C. were used. The appropriate annealing temperature for the TADG-15 and β-tubulin specific primers is 62° C.

EXAMPLE 4
T-vector ligation and transformations

The purified PCR products are ligated into the Promega T-vector plasmid and the ligation products are used to transform JM109 competent cells according to the manufacturer's instructions (Promega cat. #A3610). Positive colonies were cultured for amplification, the plasmid DNA isolated by means of the Wizard™ Minipreps DNA purification system (Promega cat #A7500), and the plasmids were digested with ApaI and SacI restriction enzymes to determine the size of the insert. Plasmids with inserts of the size(s) visualized by the previously described PCR product gel electrophoresis were sequenced.

EXAMPLE 5
DNA sequencing

Utilizing a plasmid specific primer near the cloning site, sequencing reactions were carried out using PRISM™ Ready Reaction Dye Deoxy™ terminators (Applied Biosystems cat# 401384) according to the manufacturer's instructions. Residual dye terminators were removed from the completed sequencing reaction using a Centri-sep™ spin column (Princeton Separation cat.#CS-901). An Applied Biosystems Model 373A DNA Sequencing System was available and was used for sequence analysis. Based upon the determined sequence, primers that specifically amplify the gene of interest were designed and synthesized.

EXAMPLE 6
Northern blot analysis

10 μg mRNAs were size separated by electrophoresis through a 1% formaldehyde-agarose gel in 0.02 M MOPS, 0.05 M sodium acetate (pH 7.0), and 0.001 M EDTA. The mRNAs were then blotted to Hybond-N (Amersham) by capillary action in 20×SSPE. The RNAs are fixed to the membrane by baking for 2 hours at 80° C.

Additional multiple tissue northern (MTN) blots were purchased from CLONTECH Laboratories, Inc. These blots include the Human MTN blot (cat.#7760-1), the Human MTN II blot (cat.#7759-1), the Human Fetal MTN II blot (cat.#7756-1), and the Human Brain MTN III blot (cat.#7750-1). The appropriate probes were radiolabelled utilizing the Prime-a-Gene Labeling System available from Promega (cat#U1100). The blots were probed and stripped according to the ExpressHyb Hybridization Solution protocol available from CLONTECH (cat.#8015-1 or 8015-2).

EXAMPLE 7
Quantitative PCR

Quantitative-PCR was performed in a reaction mixture consisting of cDNA derived from 50 ng of mRNA, 5 pmol of sense and antisense primers for TADG-15 and the internal control β-tubulin, 0.2 mmol of dNTPs, 0.5 mCi of [α-$^{32}$P] dCTP, and 0.625 U of Taq polymerase in 1×buffer in a final volume of 25 ml. This mixture was subjected to 1 minute of denaturation at 95° C. followed by 30 cycles of denaturation for 30 seconds at 95° C., 30 seconds of annealing at 62° C., and 1 minute of extension at 72° C. with an additional 7 minutes of extension on the last cycle. The product was electrophoresed through a 2% agarose gel for separation, the gel was dried under vacuum and autoradiographed. The relative radioactivity of each band was determined by PhosphoImager from Molecular Dynamics.

EXAMPLE 8

The present invention describes the use of primers directed to conserved areas of the serine protease family to identify members of that family which are overexpressed in carcinoma. Several genes were identified and cloned in other tissues, but not previously associated with ovarian carcinoma. The present invention describes a protease identified in ovarian carcinoma. This gene was identified using primers to the conserved area surrounding the catalytic domain of the conserved amino acid histidine and the downstream conserved amino acid serine which lies approximately 150 amino acids towards the carboxyl end of the protease.

The gene encoding the novel extracellular serine protease of the present invention was identified from a group of proteases overexpressed in carcinoma by subcloning and sequencing the appropriate PCR products. An example of such a PCR reaction is given in FIG. 1. Subcloning and sequencing of individual bands from such an amplification provided a basis for identifying the protease of the present invention.

EXAMPLE 9

The sequence determined for the catalytic domain of TADG-15 is presented in FIG. 2 and is consistent with other serine proteases and specifically contains conserved amino acids appropriate for the catalytic domain of the trypsin-like serine protease family. Specific primers (20mers) derived from this sequence were used.

Figure 3:
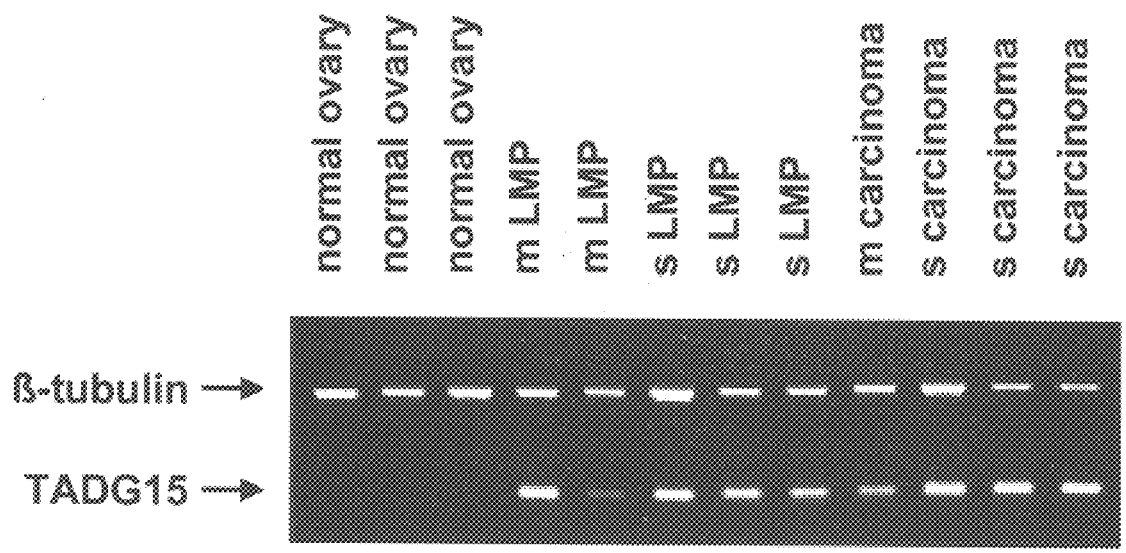
FIG. 3 shows quantitative PCR analysis of TADG-15 expression.
Figure 4:
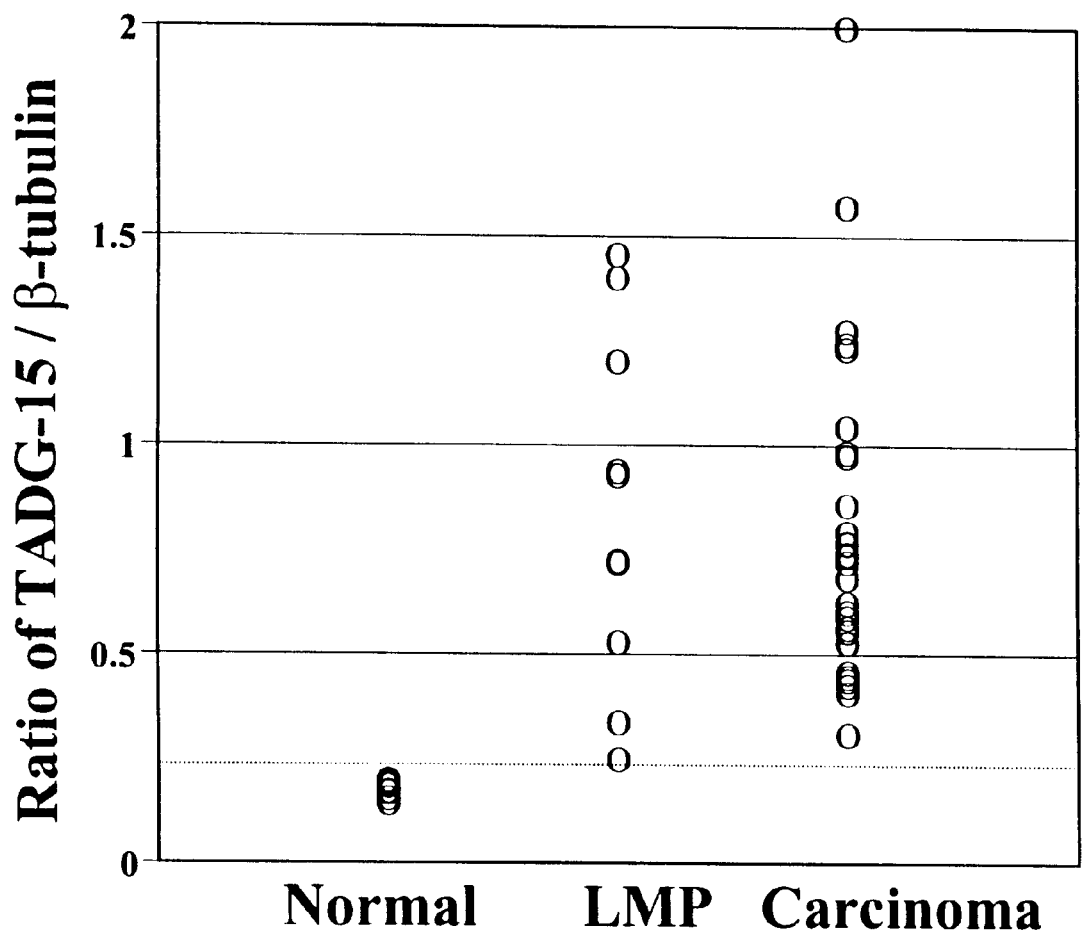
FIG. 4 shows the ratio of TADG-15 expression to expression of β-tubulin in normal tissues, low malignant potential tumors (LMP) and carcinomas.
Figure 5:
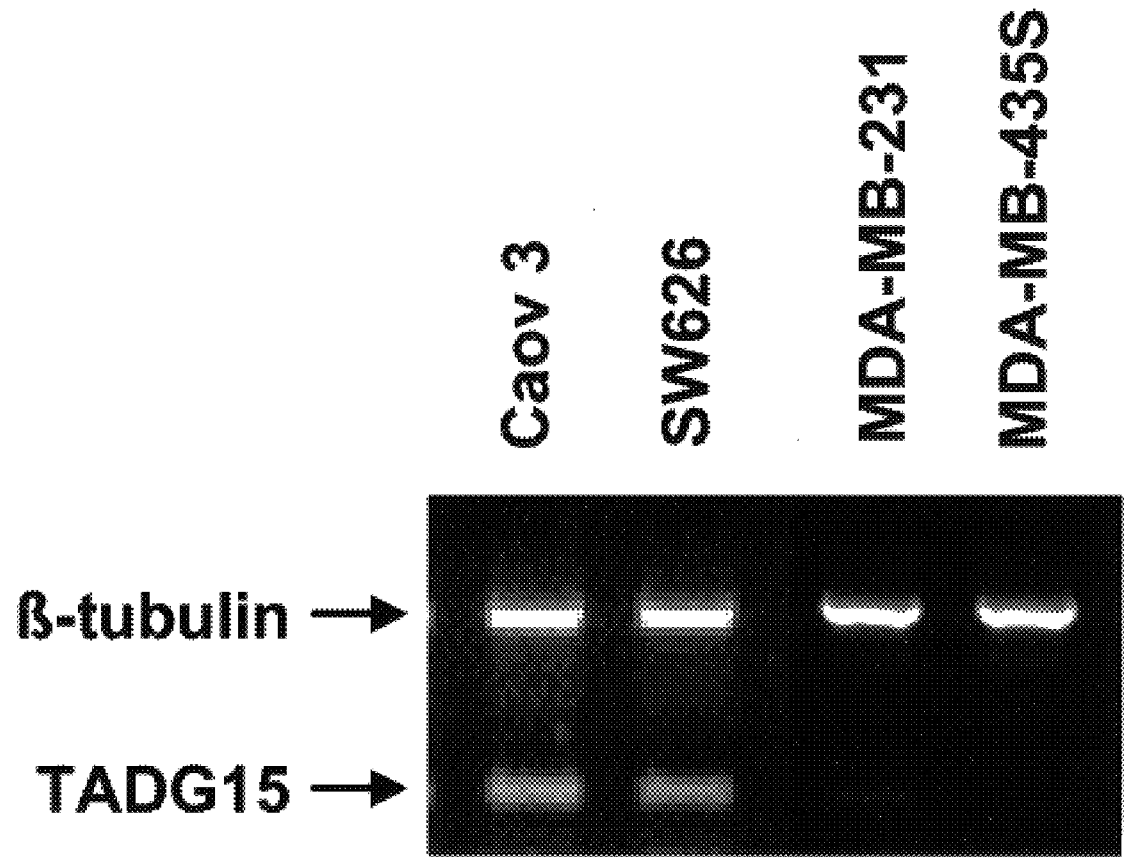
FIG. 5 shows the TADG-15 expression in tumor cell lines derived from both ovarian and breast carcinoma tissues.
Figure 6:
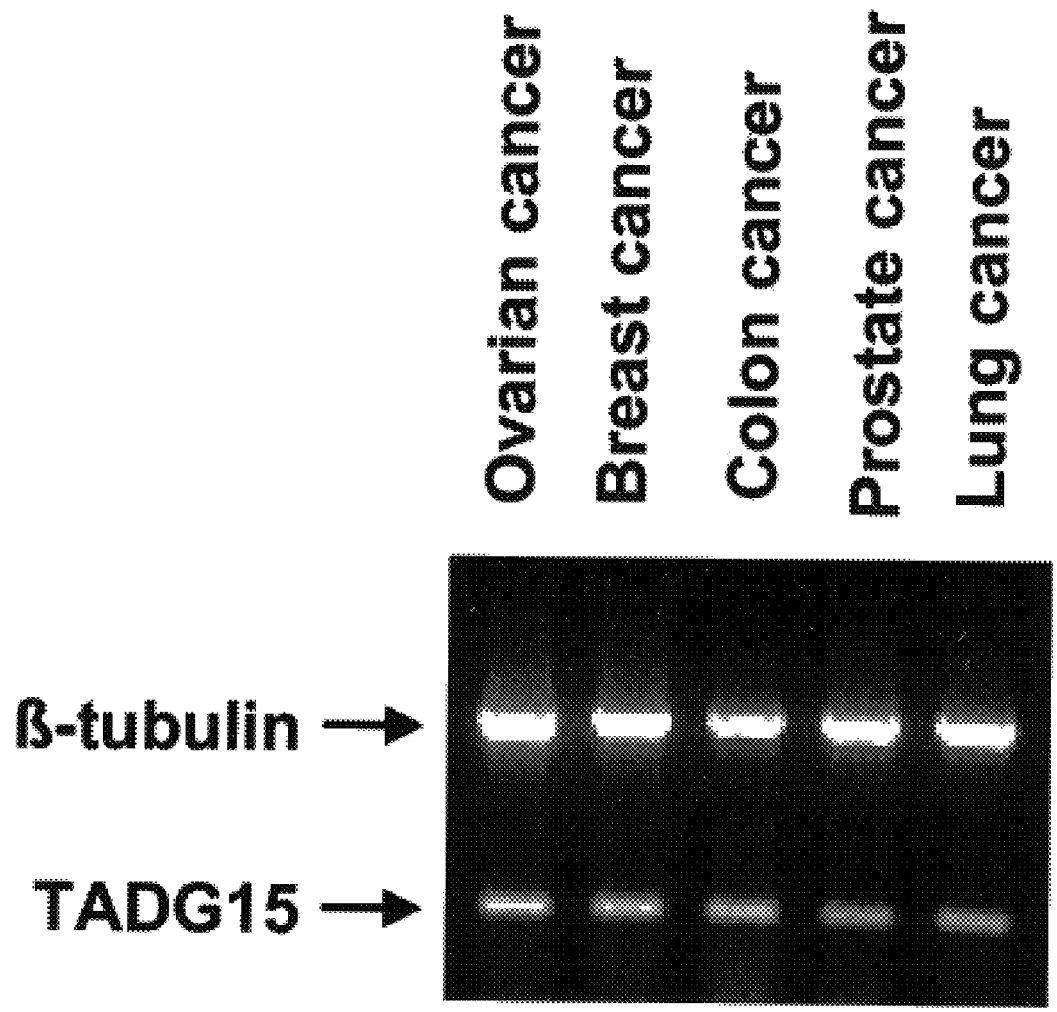
FIG. 6 shows the overexpression of TADG-15 in other tumor tissues.

A series of normal and tumor cDNAs were examined to determine the expression of the TADG-15 gene in ovarian carcinoma. In a series of normal derived cDNA compared to carcinoma derived cDNA using β-tubulin as an internal control for PCR amplification, TADG-15 was significantly overexpressed in all of the carcinomas examined and either was not detected or was detected at a very low level in normal epithelial tissue (FIG. 3). This evaluation was extended to a standard panel of about 40 tumors. Using these specific primers, the expression of this gene was also examined in tumor cell lines derived from both ovarian and breast carcinoma tissues as shown in FIG. 5 and in other tumor tissues as shown in FIG. 6. The expression of TADG-15 was also observed in carcinomas of the breast, colon, prostate and lung.

Figure 7:
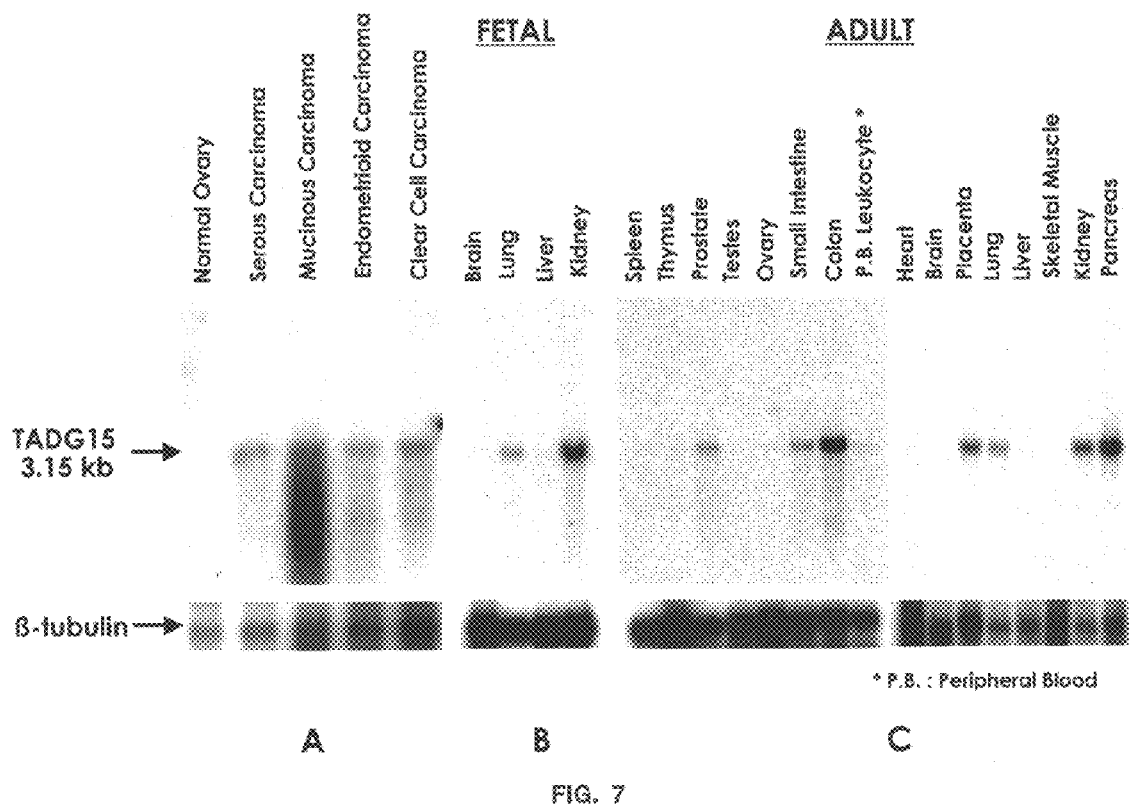
FIG. 7 shows the Northern blots of TADG-15 expression in ovarian carcinomas, fetal and normal adult tissues.
Figure 8:
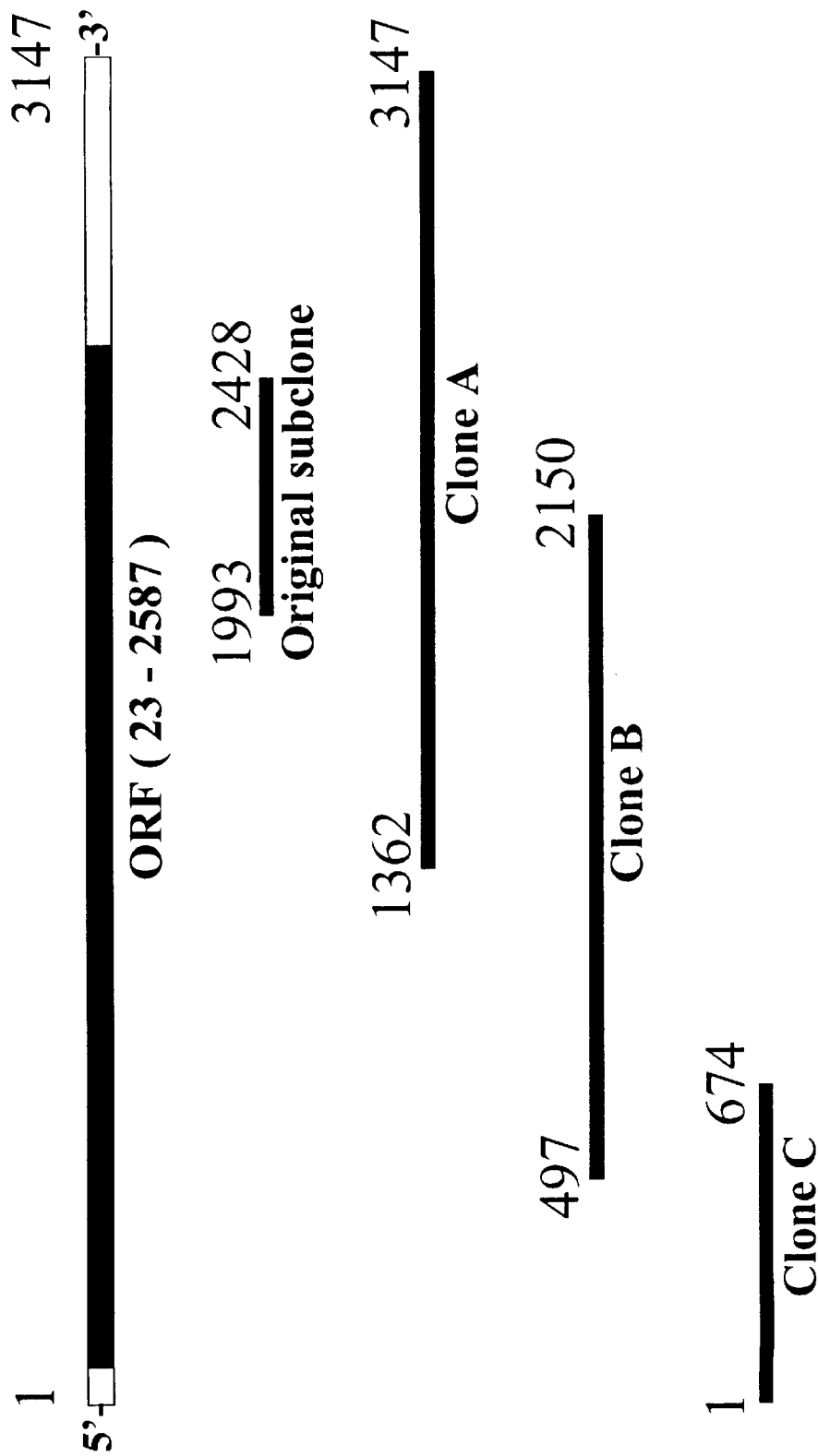
FIG. 8 shows a diagram of the TADG-15 transcript and the clones with the origin of their derivation.

Using the specific sequence for TADG-15 covering the full domain of the catalytic site as a probe for Northern blot analysis, three Northern blots were examined: one derived from ovarian tissues, both normal and carcinoma; one from fetal tissues; and one from adult normal tissues. As shown in FIG. 7, TADG-15 transcripts were noted in all ovarian carcinomas, but were not present in detectable levels in any of the following tissues: a) normal ovary, b) fetal liver and brain, c) adult spleen, thymus, testes, overy and peripheral blood lymphocytes, d) skeletal muscle, liver, brain or heart. The transcript size was found to be approximately 3.2 kb. The hybridization for the fetal and adult blots was appropriate and done with the same probe as with the ovarian tissue. Subsequent to this examination, it was confirmed that these blots contained other detectable mRNA transcripts Initially using the catalytic domain of the protease to probe Hela cDNA and ovarian tumor cDNA libraries, one clone was obtained covering the entire 3' end of the TADG-15 gene from the ovarian tumor library. On further screening using the 5' end of the newly detected clones, two more clones were identified covering the 5' end of the TADG-15 gene from the Hela library (FIG. 8). The complete nucleotide sequence (SEQ ID No: 1) is provided in FIG. 9 along with translation of the open reading frame (SEQ ID No:2).

Figure 11:
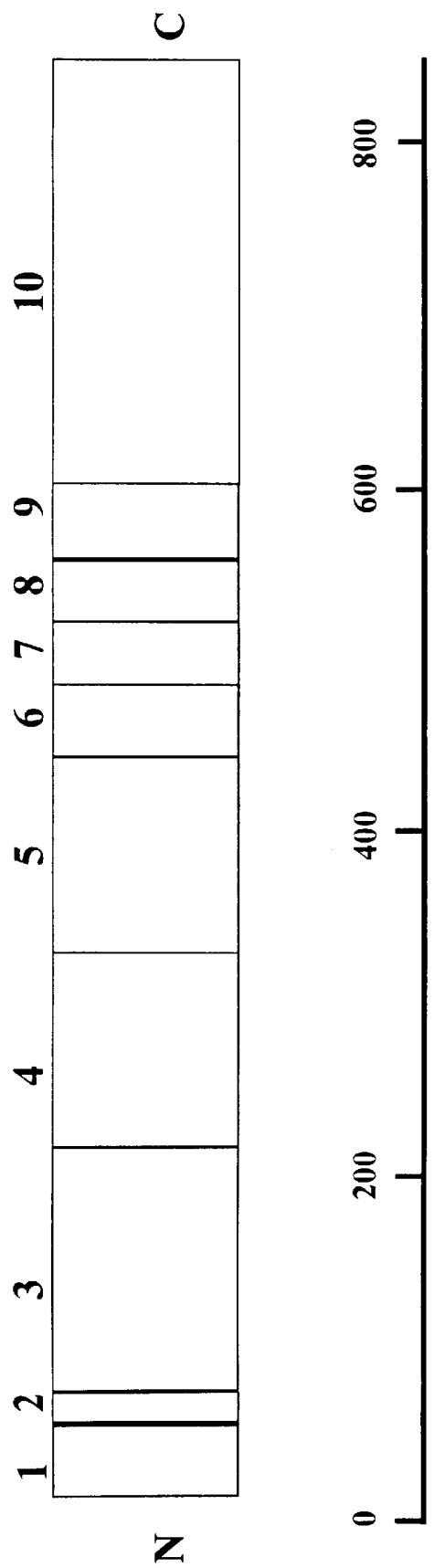
FIG. 11 shows a structure diagram of the TADG-15 protein including functional domains.

In the nucleotide sequence, there is a Kozak sequence typical of sequences upstream from the initiation site of translation. There is also a poly-adenylation signal sequence and a polyadenylated tail. The open reading frame consists of a 855 amino acid sequence (SEQ ID No:2) which includes an amino terminal cytoplasmic tail from amino acids 1–50, an approximately 22 amino acid transmembrane domain followed by an extracellular sequence preceding two CUB repeats identified from complement subcomponents Clr and Cls. These two repeats are followed by four repeat domains of a class A motif of the LDL receptor and these four repeats are followed by the protease enzyme of the trypsin family constituting the carboxyl end of the TADG-15 protein (FIG. 11). Also a clear delineation of the catalytic domain conserved histidine, aspartic acid, serine series along with a series of amino acids conserved in the serine protease family is indicated (FIG. 10).

A search of GeneBank for similar previously identified sequences yielded one such sequence with relatively high homology to a portion of the TADG-15 gene. The similarity between the portion of TADG-15 from nucleotide #182 to 3139 and SNC-19 GeneBank accession #U20428) is approximately 97% (FIG. 12). There are however significant differences between SNC-19 and TADG-15 viz. TADG-15 has an open reading frame of 855 amino acids whereas the longest ORF of SNC-19 is only 173 amino acids. SNC-19 does not include a proper start site for the initiation of translation nor does it include the amino terminal portion of the protein encoded by TADG-15. Moreover, SNC-19 does not include an ORF for a functional serine protease because the His, Asp and Ser residues necessary for function are encoded in different reading frames.

TADG-15 is a highly overexpressed gene in tumors. It is expressed in a limited number of normal tissues, primarily tissues that are involved in either uptake or secretion of molecules e.g. colon and pancreas. TADG-15 is further novel in its component structure of domains in that it has a protease catalytic domain which could be released and used as a diagnostic and which has the potential for a target for therapeutic intervention. TADG-15 also has ligand binding domains which are commonly associated with molecules that internalize or take-up ligands from the external surface of the cell as does the LDL receptor for the LDL cholesterol complex. There is potential that these domains may be involved in uptake of specific ligands and they may offer the potential for making delivery of toxic molecules or genes to tumor cells which express this molecule on their surface. It has features that are similar to the hepsin serine protease molecule in that it also has an amino-terminal transmembrane domain with the proteolytic catalytic domain extended into the extracellular matrix. The difference here is that TADG-15 includes these ligand binding repeat domains which the hepsin gene does not have. In addition to the use of this gene as a diagnostic or therapeutic target in ovarian carcinoma and other carcinomas including breast, prostate, lung and colon, its ligand-binding domains may be valuable in the uptake of specific molecules into tumor cells. Table 2 shows the number of cases with overexpression of TADG15 in normal ovaries and ovarian tumors.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

TABLE 2

Number of cases with overexpression of TADG15 in normal ovaries and ovarian tumors.

|  | N | overexpression of TADG15 | expression ratio[a] |
|---|---|---|---|
| Normal | 10 | 0 (0%) | 0.182 ± 0.024 |
| LMP | 10 | 10 (100%) | 0.847 ± 0.419 |
| serous | 6 | 6 (100%) | 0.862 ± 0.419 |
| mucinous | 4 | 4 (100%) | 0.825 ± 0.483 |
| Carcinoma | 31 | 31 (100%) | 0.771 ± 0.380 |
| serous | 18 | 18 (100%) | 0.779 ± 0.332 |
| mucinous | 7 | 7 (100%) | 0.907 ± 0.584 |
| endometrioid | 3 | 3 (100%) | 0.502 ± 0.083 |
| clear cell | 3 | 3 (100%) | 0.672 ± 0.077 |

[a]The ratio of expression level of TADG15 to β-tubulin (mean ± SD)

What is claimed is:

1. DNA encoding a Tumor Antigen Derived Gene-15 (TADG-15) protein selected from the group consisting of:
   (a) isolated DNA which encodes a TADG-15 protein;
   (b) isolated DNA which hybridizes to isolated DNA of (a) above and which encodes a TADG-15 protein; and
   (c) isolated DNA differing from the isolated DNAs of (a) and (b) above in codon sequence due to the degeneracy of the genetic code, and which encodes a TADG-15 protein.

2. The DNA of claim 1, wherein said DNA has the sequence shown in SEQ ID No:1.

3. The DNA of claim 1, wherein said TADG-15 protein has the amino acid sequence shown in SEQ ID No:2.

4. A vector comprising the DNA of claim 1 and regulatory elements necessary for expression of the DNA in a cell.

5. The vector of claim 4, wherein said DNA encodes a TADG-15 protein having the amino acid sequence shown in SEQ ID No:2.

6. A host cell transfected with the vector of claim 4, said vector expressing a TADG-15 protein.

7. The host cell of claim 6, wherein said cell is selected from group consisting of bacterial cells, mammalian cells, plant cells and insect cells.

8. The host cell of claim 7, wherein said bacterial cell is *E. coli.*

9. Isolated and purified TADG-15 protein coded for by DNA selected from the group consisting of:
   (a) isolated DNA which encodes a TADG-15 protein;
   (b) isolated DNA which hybridizes to isolated DNA of (a) above and which encodes a TADG-15 protein; and
   (c) isolated DNA differing from the isolated DNAs of (a) and (b) above in codon sequence due to the degeneracy of the genetic code, and which encodes a TADG-15 protein.

10. The isolated and purified TADG-15 protein of claim 9 having the amino acid sequence shown in SEQ ID No:2.

11. A method of detecting expression of the protein of claim 9, comprising the steps of:
    (a) contacting mRNA obtained from a cell with a labeled hybridization probe; and
    (b) detecting hybridization of the probe with the mRNA.

* * * * *

SEQUENCE LISTING

```
<160> NUMBER OF SEQ ID NOS: 13

<210> SEQ ID NO 1
<211> LENGTH: 3147
<212> TYPE: DNA
<213> ORGANISM: Homo sapiens
<220> FEATURE:
<222> LOCATION: 23..2589
<223> OTHER INFORMATION: cDNA sequence of TADG-15

<400> SEQUENCE: 1
tcaagagcgg cctcggggta ccatggggag cgatcgggcc cgcaagggcg gaggggggccc       60 gaaggacttc ggcgcgggac tcaagtacaa ctcccggcac gagaaagtga atggcttgga      120
```

```
ggaaggcgtg gagttcctgc cagtcaacaa cgtcaagaag gtggaaaagc atggcccggg      180
gcgctgggtg gtgctggcag ccgtgctgat cggcctcctc ttggtcttgc tggggatcgg      240
cttcctggtg tggcatttgc agtaccggga cgtgcgtgtc cagaaggtct tcaatggcta      300
catgaggatc acaaatgaga attttgtgga tgcctacgag aactccaact ccactgagtt      360
tgtaagcctg ccagcaagg tgaaggacgc gctgaagctg ctgtacagcg gagtcccatt      420
cctgggcccc taccacaagg agtcggctgt gacggccttc agcgagggca gcgtcatcgc      480
ctactactgg tctgagttca gcatcccgca gcacctggtg gaggaggccg agcgcgtcat      540
ggccgaggag cgcgtagtca tgctgccccc gcgggcgcgc tccctgaagt cctttgtggt      600
cacctcagtg gtggctttcc ccacggactc caaaacagta cagaggaccc aggacaacag      660
ctgcagcttt ggcctgcacg cccgcggtgt ggagctgatg cgcttcacca cgcccggctt      720
ccctgacagc ccctacccg ctcatgcccg ctgccagtgg gccctgcggg gggacgccga      780
ctcagtgctg agcctcacct tccgcagctt tgaccttgcg cctgcgacg agcgcggcag      840 cgacctggtg acggtgtaca caccctgag ccccatggag ccccacgccc tggtgcagtt      900
gtgtggcacc taccctccct cctacaacct gaccttccac tcctcccaga acgtcctgct      960
catcacactg ataaccaaca ctgagcggcg gcatcccggc tttgaggcca ccttcttcca     1020
gctgcctagg atgagcagct gtggaggccg cttacgtaaa gccagggga cattcaacag     1080 cccctactac ccaggccact acccacccaa cattgactgc acatggaaca ttgaggtgcc     1140
caacaaccag catgtgaagg tgagcttcaa attcttctac ctgctggagc ccggcgtgcc     1200
tgcgggcacc tgccccaagg actacgtgga gatcaatggg gagaaatact gcggagagag     1260
gtcccagttc gtcgtcacca gcaacagcaa caagatcaca gttcgcttcc actcagatca     1320
gtcctacacc gacaccggct tcttagctga ataccctctcc tacgactcca gtgacccatg     1380 cccgggggcag ttcacgtgcc gcacggggcg gtgtatccgg aaggagctgc gctgtgatgg     1440
ctgggccgac tgcaccgacc acagcgatga gctcaactgc agttgcgacg ccggccacca     1500
gttcacgtgc aagaacaagt tctgcaagcc cctcttctgg gtctgcgaca gtgtgaacga     1560
ctgcggagac aacagcgacg agcaggggtg cagttgtccg gcccagacct tcaggtgttc     1620
caatgggaag tgcctctcga aaagccagca gtgcaatggg aaggacgact gtggggacgg     1680
gtccgacgag gcctcctgcc ccaaggtgaa cgtcgtcact tgtaccaaac acacctaccg     1740
ctgcctcaat gggctctgct tgagcaaggg caaccctgag tgtgacggga aggaggactg     1800
tagcgacggc tcagatgaga aggactgcga ctgtgggctg cggtcattca cgagacaggc     1860
tcgtgttgtt gggggcacgg atgcggatga gggcgagtgg ccctggcagg taagcctgca     1920
tgctctgggc cagggccaca tctgcggtgc ttccctcatc tctcccaact ggctggtctc     1980
tgccgcacac tgctacatcg atgacagagg attcaggtac tcagaccccca cgcagtggac     2040 ggccttcctg ggcttgcacg accagagcca gcgcagcgcc cctgggtgc aggagcgcag     2100 gctcaagcgc atcatctccc acccccttctt caatgacttc accttcgact atgacatcgc     2160
gctgctggag ctggagaaac cggcagagta cagctccatg gtgcgcccca tctgcctgcc     2220
ggacgcctcc catgtcttcc ctgccggcaa ggccatctgg gtcacgggct ggggacacac     2280
ccagtatgga ggcactggcg cgctgatcct gcaaaagggt gagatccgcg tcatcaacca     2340
gaccacctgc gagaacctcc tgccgcagca gatcacgccg cgcatgatgt gcgtgggctt     2400
cctcagcggc ggcgtggact cctgccaggg tgattccggg ggacccctgt ccagcgtgga     2460
ggcggatggg cggatcttcc aggccggtgt ggtgagctgg ggagacggct gcgctcagag     2520
```

-continued

```
gaacaagcca ggcgtgtaca caaggctccc tctgtttcgg gactggatca aagagaacac    2580
tggggtatag gggccggggc cacccaaatg tgtacacctg cggggccacc catcgtccac    2640
cccagtgtgc acgcctgcag gctggagact ggaccgctga ctgcaccagc gcccccagaa    2700
catacactgt gaactcaatc tccagggctc caaatctgcc tagaaaacct ctcgcttcct    2760
cagcctccaa agtggagctg ggaggtagaa ggggaggaca ctggtggttc tactgaccca    2820
actgggggca aagtttgaa gacacagcct cccccgccag cccaagctg ggccgaggcg    2880 cgtttgtgta tatctgcctc ccctgtctgt aaggagcagc gggaacggag cttcggagcc    2940
tcctcagtga aggtggtggg gctgccggat ctgggctgtg gggcccttgg ccacgctct    3000 tgaggaagcc caggctcgga ggaccctgga aaacagacgg gtctgagact gaaattgttt    3060
taccagctcc cagggtggac ttcagtgtgt gtatttgtgt aaatgggtaa aacaatttat    3120 ttcttttaa aaaaaaaaa aaaaaa                                           3147
```

<210> SEQ ID NO 2
<211> LENGTH: 855
<212> TYPE: PRT
<213> ORGANISM: Homo sapiens
<220> FEATURE:
<223> OTHER INFORMATION: Amino acid sequence of TADG-15 encoded by
      nucleotides 23 to 2589 of Sequence 1

<400> SEQUENCE: 2

```
Met Gly Ser Asp Arg Ala Arg Lys Gly Gly Gly Pro Lys Asp
            5                   10                  15

Phe Gly Ala Gly Leu Lys Tyr Asn Ser Arg His Glu Lys Val Asn
                20                  25                  30

Gly Leu Glu Glu Gly Val Glu Phe Leu Pro Val Asn Asn Val Lys
                35                  40                  45

Lys Val Glu Lys His Gly Pro Gly Arg Trp Val Val Leu Ala Ala
                50                  55                  60

Val Leu Ile Gly Leu Leu Val Leu Gly Ile Gly Phe Leu
                65                  70                  75

Val Trp His Leu Gln Tyr Arg Asp Val Arg Val Gln Lys Val Phe
                80                  85                  90

Asn Gly Tyr Met Arg Ile Thr Asn Glu Asn Phe Val Asp Ala Tyr
                95                  100                 105

Glu Asn Ser Asn Ser Thr Glu Phe Val Ser Leu Ala Ser Lys Val
                110                 115                 120

Lys Asp Ala Leu Lys Leu Leu Tyr Ser Gly Val Pro Phe Leu Gly
                125                 130                 135

Pro Tyr His Lys Glu Ser Ala Val Thr Ala Phe Ser Glu Gly Ser
                140                 145                 150

Val Ile Ala Tyr Tyr Trp Ser Glu Phe Ser Ile Pro Gln His Leu
                155                 160                 165

Val Glu Glu Ala Glu Arg Val Met Ala Glu Glu Arg Val Val Met
                170                 175                 180

Leu Pro Pro Arg Ala Arg Ser Leu Lys Ser Phe Val Val Thr Ser
                185                 190                 195

Val Val Ala Phe Pro Thr Asp Ser Lys Thr Val Gln Arg Thr Gln
                200                 205                 210

Asp Asn Ser Cys Ser Phe Gly Leu His Ala Arg Gly Val Glu Leu
                215                 220                 225

Met Arg Phe Thr Thr Pro Gly Phe Pro Asp Ser Pro Tyr Pro Ala
                230                 235                 240
```

-continued

```
His Ala Arg Cys Gln Trp Ala Leu Arg Gly Asp Ala Asp Ser Val
            245                 250                 255
Leu Ser Leu Thr Phe Arg Ser Phe Asp Leu Ala Ser Cys Asp Glu
            260                 265                 270
Arg Gly Ser Asp Leu Val Thr Val Tyr Asn Thr Leu Ser Pro Met
            275                 280                 285
Glu Pro His Ala Leu Val Gln Leu Cys Gly Thr Tyr Pro Pro Ser
            290                 295                 300
Tyr Asn Leu Thr Phe His Ser Ser Gln Asn Val Leu Leu Ile Thr
            305                 310                 315
Leu Ile Thr Asn Thr Glu Arg Arg His Pro Gly Phe Glu Ala Thr
            320                 325                 330
Phe Phe Gln Leu Pro Arg Met Ser Ser Cys Gly Gly Arg Leu Arg
            335                 340                 345
Lys Ala Gln Gly Thr Phe Asn Ser Pro Tyr Tyr Pro Gly His Tyr
            350                 355                 360
Pro Pro Asn Ile Asp Cys Thr Trp Asn Ile Glu Val Pro Asn Asn
            365                 370                 375
Gln His Val Lys Val Ser Phe Lys Phe Tyr Leu Leu Glu Pro
            380                 385                 390
Gly Val Pro Ala Gly Thr Cys Pro Lys Asp Tyr Val Glu Ile Asn
            395                 400                 405
Gly Glu Lys Tyr Cys Gly Glu Arg Ser Gln Phe Val Val Thr Ser
            410                 415                 420
Asn Ser Asn Lys Ile Thr Val Arg Phe His Ser Asp Gln Ser Tyr
            425                 430                 435
Thr Asp Thr Gly Phe Leu Ala Glu Tyr Leu Ser Tyr Asp Ser Ser
            440                 445                 450
Asp Pro Cys Pro Gly Gln Phe Thr Cys Arg Thr Gly Arg Cys Ile
            455                 460                 465
Arg Lys Glu Leu Arg Cys Asp Gly Trp Ala Asp Cys Thr Asp His
            470                 475                 480
Ser Asp Glu Leu Asn Cys Ser Cys Asp Ala Gly His Gln Phe Thr
            485                 490                 495
Cys Lys Asn Lys Phe Cys Lys Pro Leu Phe Trp Val Cys Asp Ser
            500                 505                 510
Val Asn Asp Cys Gly Asp Asn Ser Asp Glu Gln Gly Cys Ser Cys
            515                 520                 525
Pro Ala Gln Thr Phe Arg Cys Ser Asn Gly Lys Cys Leu Ser Lys
            530                 535                 540
Ser Gln Gln Cys Asn Gly Lys Asp Asp Cys Gly Asp Gly Ser Asp
            545                 550                 555
Glu Ala Ser Cys Pro Lys Val Asn Val Val Thr Cys Thr Lys His
            560                 565                 570
Thr Tyr Arg Cys Leu Asn Gly Leu Cys Leu Ser Lys Gly Asn Pro
            575                 580                 585
Glu Cys Asp Gly Lys Glu Asp Cys Ser Asp Gly Ser Asp Glu Lys
            590                 595                 600
Asp Cys Asp Cys Gly Leu Arg Ser Phe Thr Arg Gln Ala Arg Val
            605                 610                 615
Val Gly Gly Thr Asp Ala Asp Glu Gly Glu Trp Pro Trp Gln Val
            620                 625                 630
Ser Leu His Ala Leu Gly Gln Gly His Ile Cys Gly Ala Ser Leu
```

```
                    635                 640                 645
Ile Ser Pro Asn Trp Leu Val Ser Ala Ala His Cys Tyr Ile Asp
            650                 655                 660
Asp Arg Gly Phe Arg Tyr Ser Asp Pro Thr Gln Trp Thr Ala Phe
            665                 670                 675
Leu Gly Leu His Asp Ser Gln Arg Ser Ala Pro Gly Val Gln
            680                 685                 690
Glu Arg Arg Leu Lys Arg Ile Ile Ser His Pro Phe Phe Asn Asp
            695                 700                 705
Phe Thr Phe Asp Tyr Asp Ile Ala Leu Leu Glu Leu Glu Lys Pro
            710                 715                 720
Ala Glu Tyr Ser Ser Met Val Arg Pro Ile Cys Leu Pro Asp Ala
            725                 730                 735
Ser His Val Phe Pro Ala Gly Lys Ala Ile Trp Val Thr Gly Trp
            740                 745                 750
Gly His Thr Gln Tyr Gly Gly Thr Gly Ala Leu Ile Leu Gln Lys
            755                 760                 765
Gly Glu Ile Arg Val Ile Asn Gln Thr Thr Cys Glu Asn Leu Leu
            770                 775                 780
Pro Gln Gln Ile Thr Pro Arg Met Met Cys Val Gly Phe Leu Ser
            785                 790                 795
Gly Gly Val Asp Ser Cys Gln Gly Asp Ser Gly Gly Pro Leu Ser
            800                 805                 810
Ser Val Glu Ala Asp Gly Arg Ile Phe Gln Ala Gly Val Val Ser
            815                 820                 825
Trp Gly Asp Gly Cys Ala Gln Arg Asn Lys Pro Gly Val Tyr Thr
            830                 835                 840
Arg Leu Pro Leu Phe Arg Asp Trp Ile Lys Glu Asn Thr Gly Val
            845                 850                 855

<210> SEQ ID NO 3
<211> LENGTH: 256
<212> TYPE: PRT
<213> ORGANISM: Unknown
<220> FEATURE:
<223> OTHER INFORMATION: Serine protease catalytic domain of hepsin
      (Heps) homologous to similar domain in TADG-15

<400> SEQUENCE: 3

Arg Ile Val Gly Gly Arg Asp Thr Ser Leu Gly Arg Trp Pro Trp
              5                  10                  15
Gln Val Ser Leu Arg Tyr Asp Gly Ala His Leu Cys Gly Gly Ser
             20                  25                  30
Leu Leu Ser Gly Asp Trp Val Leu Thr Ala Ala His Cys Phe Pro
             35                  40                  45
Glu Arg Asn Arg Val Leu Ser Arg Trp Arg Val Phe Ala Gly Ala
             50                  55                  60
Val Ala Gln Ala Ser Pro His Gly Leu Gln Leu Gly Val Gln Ala
             65                  70                  75
Val Val Tyr His Gly Gly Tyr Leu Pro Phe Arg Asp Pro Asn Ser
             80                  85                  90
Glu Glu Asn Ser Asn Asp Ile Ala Leu Val His Leu Ser Ser Pro
             95                 100                 105
Leu Pro Leu Thr Glu Tyr Ile Gln Pro Val Cys Leu Pro Ala Ala
            110                 115                 120
Gly Gln Ala Leu Val Asp Gly Lys Ile Cys Thr Val Thr Gly Trp
```

```
                         125                 130                 135

Gly Asn Thr Gln Tyr Tyr Gly Gln Gln Ala Gly Val Leu Gln Glu
                140                 145                 150

Ala Arg Val Pro Ile Ile Ser Asn Asp Val Cys Asn Gly Ala Asp
                155                 160                 165

Phe Tyr Gly Asn Gln Ile Lys Pro Lys Met Phe Cys Ala Gly Tyr
                170                 175                 180

Pro Glu Gly Gly Ile Asp Ala Cys Gln Gly Asp Ser Gly Gly Pro
                185                 190                 195

Phe Val Cys Glu Asp Ser Ile Ser Arg Thr Pro Arg Trp Arg Leu
                200                 205                 210

Cys Gly Ile Val Ser Trp Gly Thr Gly Cys Ala Leu Ala Gln Lys
                215                 220                 225

Pro Gly Val Tyr Thr Lys Val Ser Asp Phe Arg Glu Trp Ile Phe
                230                 235                 240

Gln Ala Ile Lys Thr His Ser Glu Ala Ser Gly Met Val Thr Gln
                245                 250                 255

Leu

<210> SEQ ID NO 4
<211> LENGTH: 225
<212> TYPE: PRT
<213> ORGANISM: Unknown
<220> FEATURE:
<223> OTHER INFORMATION: Serine protease catalytic domain of Scce
      homologous to similar domain in TADG-15

<400> SEQUENCE: 4

Lys Ile Ile Asp Gly Ala Pro Cys Ala Arg Gly Ser His Pro Trp
                  5                  10                  15

Gln Val Ala Leu Leu Ser Gly Asn Gln Leu His Cys Gly Gly Val
                 20                  25                  30

Leu Val Asn Glu Arg Trp Val Leu Thr Ala Ala His Cys Lys Met
                 35                  40                  45

Asn Glu Tyr Thr Val His Leu Gly Ser Asp Thr Leu Gly Asp Arg
                 50                  55                  60

Arg Ala Gln Arg Ile Lys Ala Ser Lys Ser Phe Arg His Pro Gly
                 65                  70                  75

Tyr Ser Thr Gln Thr His Val Asn Asp Leu Met Leu Val Lys Leu
                 80                  85                  90

Asn Ser Gln Ala Arg Leu Ser Ser Met Val Lys Lys Val Arg Leu
                 95                 100                 105

Pro Ser Arg Cys Glu Pro Pro Gly Thr Thr Cys Thr Val Ser Gly
                110                 115                 120

Trp Gly Thr Thr Thr Ser Pro Asp Val Thr Phe Pro Ser Asp Leu
                125                 130                 135

Met Cys Val Asp Val Lys Leu Ile Ser Pro Gln Asp Cys Thr Lys
                140                 145                 150

Val Tyr Lys Asp Leu Leu Glu Asn Ser Met Leu Cys Ala Gly Ile
                155                 160                 165

Pro Asp Ser Lys Lys Asn Ala Cys Asn Gly Asp Ser Gly Gly Pro
                170                 175                 180

Leu Val Cys Arg Gly Thr Leu Gln Gly Leu Val Ser Trp Gly Thr
                185                 190                 195

Phe Pro Cys Gly Gln Pro Asn Asp Pro Gly Val Tyr Thr Gln Val
                200                 205                 210
```

```
Cys Lys Phe Thr Lys Trp Ile Asn Asp Thr Met Lys Lys His Arg
            215                 220                 225

<210> SEQ ID NO 5
<211> LENGTH: 225
<212> TYPE: PRT
<213> ORGANISM: Unknown
<220> FEATURE:
<223> OTHER INFORMATION: Serine protease catalytic domain of trypsin
      (Try) homologous to similar domain in TADG-15

<400> SEQUENCE: 5

Lys Ile Val Gly Gly Tyr Asn Cys Glu Glu Asn Ser Val Pro Tyr
              5                  10                  15

Gln Val Ser Leu Asn Ser Gly Tyr His Phe Cys Gly Gly Ser Leu
             20                  25                  30

Ile Asn Glu Gln Trp Val Val Ser Ala Gly His Cys Tyr Lys Ser
             35                  40                  45

Arg Ile Gln Val Arg Leu Gly Glu His Asn Ile Glu Val Leu Glu
             50                  55                  60

Gly Asn Glu Gln Phe Ile Asn Ala Ala Lys Ile Ile Arg His Pro
             65                  70                  75

Gln Tyr Asp Arg Lys Thr Leu Asn Asn Asp Ile Met Leu Ile Lys
             80                  85                  90

Leu Ser Ser Arg Ala Val Ile Asn Ala Arg Val Ser Thr Ile Ser
             95                 100                 105

Leu Pro Thr Ala Pro Pro Ala Thr Gly Thr Lys Cys Leu Ile Ser
            110                 115                 120

Gly Trp Gly Asn Thr Ala Ser Ser Gly Ala Asp Tyr Pro Asp Glu
            125                 130                 135

Leu Gln Cys Leu Asp Ala Pro Val Leu Ser Gln Ala Lys Cys Glu
            140                 145                 150

Ala Ser Tyr Pro Gly Lys Ile Thr Ser Asn Met Phe Cys Val Gly
            155                 160                 165

Phe Leu Glu Gly Gly Lys Asp Ser Cys Gln Gly Asp Ser Gly Gly
            170                 175                 180

Pro Val Val Cys Asn Gly Gln Leu Gln Gly Val Val Ser Trp Gly
            185                 190                 195

Asp Gly Cys Ala Gln Lys Asn Lys Pro Gly Val Tyr Thr Lys Val
            200                 205                 210

Tyr Asn Tyr Val Lys Trp Ile Lys Asn Thr Ile Ala Ala Asn Ser
            215                 220                 225

<210> SEQ ID NO 6
<211> LENGTH: 231
<212> TYPE: PRT
<213> ORGANISM: Unknown
<220> FEATURE:
<223> OTHER INFORMATION: Serine protease catalytic domain of
      chymotrypsin (Chymb) homologous to similar domain in TADG-15

<400> SEQUENCE: 6

Arg Ile Val Asn Gly Glu Asp Ala Val Pro Gly Ser Trp Pro Trp
              5                  10                  15

Gln Val Ser Leu Gln Asp Lys Thr Gly Phe His Phe Cys Gly Gly
             20                  25                  30

Ser Leu Ile Ser Glu Asp Trp Val Val Thr Ala Ala His Cys Gly
             35                  40                  45
```

```
Val Arg Thr Ser Asp Val Val Ala Gly Glu Phe Asp Gln Gly
            50                  55                  60

Ser Asp Glu Glu Asn Ile Gln Val Leu Lys Ile Ala Lys Val Phe
            65                  70                  75

Lys Asn Pro Lys Phe Ser Ile Leu Thr Val Asn Asn Asp Ile Thr
            80                  85                  90

Leu Leu Lys Leu Ala Thr Pro Ala Arg Phe Ser Gln Thr Val Ser
            95                 100                 105

Ala Val Cys Leu Pro Ser Ala Asp Asp Phe Pro Ala Gly Thr
           110                 115                 120

Leu Cys Ala Thr Thr Gly Trp Gly Lys Thr Lys Tyr Asn Ala Asn
           125                 130                 135

Lys Thr Pro Asp Lys Leu Gln Gln Ala Ala Leu Pro Leu Leu Ser
           140                 145                 150

Asn Ala Glu Cys Lys Lys Ser Trp Gly Arg Arg Ile Thr Asp Val
           155                 160                 165

Met Ile Cys Ala Gly Ala Ser Gly Val Ser Ser Cys Met Gly Asp
           170                 175                 180

Ser Gly Gly Pro Leu Val Cys Gln Lys Asp Gly Ala Trp Thr Leu
           185                 190                 195

Val Gly Ile Val Ser Trp Gly Ser Asp Thr Cys Ser Thr Ser Ser
           200                 205                 210

Pro Gly Val Tyr Ala Arg Val Thr Lys Leu Ile Pro Trp Val Gln
           215                 220                 225

Lys Ile Leu Ala Ala Asn
           230

<210> SEQ ID NO 7
<211> LENGTH: 255
<212> TYPE: PRT
<213> ORGANISM: Unknown
<220> FEATURE:
<223> OTHER INFORMATION: Serine protease catalytic domain of factor 7
      (Fac7) homologous to similar domain in TADG-15

<400> SEQUENCE: 7

Arg Ile Val Gly Gly Lys Val Cys Pro Lys Gly Glu Cys Pro Trp
             5                  10                  15

Gln Val Leu Leu Leu Val Asn Gly Ala Gln Leu Cys Gly Gly Thr
            20                  25                  30

Leu Ile Asn Thr Ile Trp Val Val Ser Ala Ala His Cys Phe Asp
            35                  40                  45

Lys Ile Lys Asn Trp Arg Asn Leu Ile Ala Val Leu Gly Glu His
            50                  55                  60

Asp Leu Ser Glu His Asp Gly Asp Glu Gln Ser Arg Arg Val Ala
            65                  70                  75

Gln Val Ile Ile Pro Ser Thr Tyr Val Pro Gly Thr Thr Asn His
            80                  85                  90

Asp Ile Ala Leu Leu Arg Leu His Gln Pro Val Val Leu Thr Asp
            95                 100                 105

His Val Val Pro Leu Cys Leu Pro Glu Arg Thr Phe Ser Glu Arg
           110                 115                 120

Thr Leu Ala Phe Val Arg Phe Ser Leu Val Ser Gly Trp Gly Gln
           125                 130                 135

Leu Leu Asp Arg Gly Ala Thr Ala Leu Glu Leu Met Val Leu Asn
           140                 145                 150
```

```
Val Pro Arg Leu Met Thr Gln Asp Cys Leu Gln Gln Ser Arg Lys
            155                 160                 165

Val Gly Asp Ser Pro Asn Ile Thr Glu Tyr Met Phe Cys Ala Gly
            170                 175                 180

Tyr Ser Asp Gly Ser Lys Asp Ser Cys Lys Gly Asp Ser Gly Gly
            185                 190                 195

Pro His Ala Thr His Tyr Arg Gly Thr Trp Tyr Leu Thr Gly Ile
            200                 205                 210

Val Ser Trp Gly Gln Gly Cys Ala Thr Val Gly His Phe Gly Val
            215                 220                 225

Tyr Thr Arg Val Ser Gln Tyr Ile Glu Trp Leu Gln Lys Leu Met
            230                 235                 240

Arg Ser Glu Pro Arg Pro Gly Val Leu Leu Arg Ala Pro Phe Pro
            245                 250                 255

<210> SEQ ID NO 8
<211> LENGTH: 253
<212> TYPE: PRT
<213> ORGANISM: Unknown
<220> FEATURE:
<223> OTHER INFORMATION: Serine protease catalytic domain of tissue
      plasminogen activator (Tpa) homologous to similar domain in
      TADG-15

<400> SEQUENCE: 8

Arg Ile Lys Gly Gly Leu Phe Ala Asp Ile Ala Ser His Pro Trp
              5                  10                  15

Gln Ala Ala Ile Phe Ala Lys His Arg Arg Ser Pro Gly Glu Arg
             20                  25                  30

Phe Leu Cys Gly Gly Ile Leu Ile Ser Ser Cys Trp Ile Leu Ser
             35                  40                  45

Ala Ala His Cys Phe Gln Glu Arg Phe Pro Pro His His Leu Thr
             50                  55                  60

Val Ile Leu Gly Arg Thr Tyr Arg Val Val Pro Gly Glu Glu Glu
             65                  70                  75

Gln Lys Phe Glu Val Glu Lys Tyr Ile Val His Lys Glu Phe Asp
             80                  85                  90

Asp Asp Thr Tyr Asp Asn Asp Ile Ala Leu Leu Gln Leu Lys Ser
             95                 100                 105

Asp Ser Ser Arg Cys Ala Gln Glu Ser Ser Val Val Arg Thr Val
            110                 115                 120

Cys Leu Pro Pro Ala Asp Leu Gln Leu Pro Asp Trp Thr Glu Cys
            125                 130                 135

Glu Leu Ser Gly Tyr Gly Lys His Glu Ala Leu Ser Pro Phe Tyr
            140                 145                 150

Ser Glu Arg Leu Lys Glu Ala His Val Arg Leu Tyr Pro Ser Ser
            155                 160                 165

Arg Cys Thr Ser Gln His Leu Leu Asn Arg Thr Val Thr Asp Asn
            170                 175                 180

Met Leu Cys Ala Gly Asp Thr Arg Ser Gly Gly Pro Gln Ala Asn
            185                 190                 195

Leu His Asp Ala Cys Gln Gly Asp Ser Gly Gly Pro Leu Val Cys
            200                 205                 210

Leu Asn Asp Gly Arg Met Thr Leu Val Gly Ile Ile Ser Trp Gly
            215                 220                 225

Leu Gly Cys Gly Gln Lys Asp Val Pro Gly Val Tyr Thr Lys Val
            230                 235                 240
```

-continued

Thr Asn Tyr Leu Asp Trp Ile Arg Asp Asn Met Arg Pro
                245                 250

<210> SEQ ID NO 9
<211> LENGTH: 2900
<212> TYPE: DNA
<213> ORGANISM: Homo sapiens
<220> FEATURE:
<223> OTHER INFORMATION: SNC19 mRNA sequence (U20428)

<400> SEQUENCE: 9

| | | | | | |
|---|---|---|---|---|---|
| cgctgggtgg | tgctggcagc | cgtgctgatc | ggcctcctct | tggtcttgct | ggggatcggc | 60 |
| ttcctggtgt | ggcatttgca | gtaccgggac | gtgcgtgtcc | agaaggtctt | caatggctac | 120 |
| atgaggatca | caaatgagaa | ttttgtggat | gcctacgaga | actccaactc | cactgagttt | 180 |
| gtaagcctgg | ccagcaaggt | gaaggacgcg | ctgaagctgc | tgtacagcgg | agtcccattc | 240 |
| ctgggcccct | accacaagga | gtcggctgtg | acggccttca | gcgagggcag | cgtcatcgcc | 300 |
| tactactggt | ctgagttcag | catcccgcag | cacctggttg | aggaggccga | gcgcgtcatg | 360 |
| gccaggagcg | cgtagtcatg | ctgccccgc | gggcgcgctc | cctgaagtcc | tttgtggtca | 420 |
| cctcagtggt | ggctttcccc | acggactcca | aaacagtaca | gaggacccag | gacaacagct | 480 |
| gcagctttgg | cctgcacgcc | gcggtgtgga | gctgatgcgc | ttcaccacgc | cggcttccct | 540 |
| gacagcccct | accccgctca | tgcccgctgc | cagtgggctg | cggggacgcg | acgcagtgct | 600 |
| gagctactcg | agctgactcg | cagcttgact | gcgcctcgac | gagcgcggca | gcgacctggt | 660 |
| gacgtgtaca | acaccctgag | ccccatggag | ccccacgcct | ggtgagtgtg | tggcacctac | 720 |
| cctccctcct | acaacctgac | cttccactcc | ctcccacgaa | cgtcctgctc | atcacactga | 780 |
| taaccaacac | tgacgcggca | tcccggcttt | gaggccacct | tcttccagct | gcctaggatg | 840 |
| agcagctgtg | gaggccgctt | acgtaaagcc | caggggacat | tcaacagccc | ctactaccca | 900 |
| ggccactacc | cacccaacat | tgactgcaca | tggaaaattg | aggtgcccaa | caaccagcat | 960 |
| gtgaaggtgc | gcttcaaatt | cttctacctg | ctggagcccg | cgtgcctgc | gggcacctgc | 1020 |
| cccaaggact | acgtggagat | caatggggag | aaatactgcg | gagagaggtc | ccagttcgtc | 1080 |
| gtcaccagca | acagcaacaa | gatcacagtt | cgcttccact | cagatcagtc | ctacaccgac | 1140 |
| accggcttct | tagctgaata | cctctcctac | gactccagtg | acccatgccc | ggggcagttc | 1200 |
| acgtgccgca | cggggcggtg | tatccggaag | gagctgcgct | gtgatggctg | ggcgactgca | 1260 |
| ccgaccacag | cgatgagctc | aactgcagtt | gcgacgccgg | ccaccagttc | acgtgcaaga | 1320 |
| gcaagttctg | caagctcttc | tgggtctgcg | acagtgtgaa | cgagtgcgga | gacaacagcg | 1380 |
| acgagcaggg | ttgcatttgt | ccggacccag | accttcaggt | gttccaatgg | gaagtgcctc | 1440 |
| tcgaaaagcc | agcagtgcaa | tggaaggac | gactgtgggg | acgggtccga | cgaggcctcc | 1500 |
| tgccccaagg | tgaacgtcgt | cacttgtacc | aaacacacct | accgctgcct | caatgggctc | 1560 |
| tgcttgagca | agggcaaccc | tgagtgtgac | gggaaggagg | actgtagcga | cggctcagat | 1620 |
| gagaaggact | gcgactgtgg | gctgcggtca | ttcacgagac | aggctcgtgt | tgttgggggc | 1680 |
| acggatgcgg | atgagggcga | gtgggccctgg | caggtaagcc | tgcatgctct | gggccagggc | 1740 |
| cacatctgcg | gtgcttccct | catctctccc | aactggctgg | tctctgccgc | acactgctac | 1800 |
| atcgatgaca | gaggattcag | gtactcagac | cccacgcagg | acggccttcc | tgggcttgca | 1860 |
| cgaccagagc | cagcgcaggc | cctggggtgc | aggagcgcag | gctcaagcgc | atcatctccc | 1920 |
| accccttctt | caatgacttc | accttcgact | atgacatcgc | gctgctggag | ctggagaaac | 1980 |

```
cggcagagta cagctccatg gtgcggccca tctgcctgcc ggacgcctgc catgtcttcc    2040
ctgccggcaa ggccatctgg gtcacgggct ggggacacac ccagtatgga ggcactggcg    2100
cgctgatcct gcaaaagggt gagatccgcg tcatcaacca gaccacctgc gagaacctcc    2160
tgccgcagca gatcacgccg cgcatgatgt gcgtgggctt cctcagcggc ggcgtggact    2220
cctgccaggg tgattccggg ggaccccctgt ccagcgtgga ggcggatggg cggatcttcc    2280
```

-continued

```
<212> TYPE: DNA
<213> ORGANISM: Artificial Sequence
<220> FEATURE:
<221> NAME/KEY: primer_bind
<222> LOCATION: 1-17
<223> OTHER INFORMATION: Forward primer for analysis of B-tubulin mRNA
      expression by quantitative PCR.

<400> SEQUENCE: 13
ctgtcttgac attgttg                                                    17
```